(12) United States Patent
Wang et al.

(10) Patent No.: US 8,396,535 B2
(45) Date of Patent: Mar. 12, 2013

(54) INTEGRATED OPTICAL SCANNING IMAGE ACQUISITION AND DISPLAY

(75) Inventors: Wei-Chih Wang, Sammamish, WA (US); Eric Seibel, Seattle, WA (US); Per Reinhall, Seattle, WA (US); Mark Fauver, Seattle, WA (US); Chris Brown, Seattle, WA (US)

(73) Assignee: University of Washington, Seattle, WA (US)

( * ) Notice: Subject to any disclaimer, the term of this patent is extended or adjusted under 35 U.S.C. 154(b) by 548 days.

(21) Appl. No.: 12/434,129

(22) Filed: May 1, 2009

(65) Prior Publication Data

US 2009/0235396 A1   Sep. 17, 2009

Related U.S. Application Data

(63) Continuation of application No. 10/655,482, filed on Sep. 4, 2003, now Pat. No. 7,555,333, which is a continuation-in-part of application No. 09/850,594, filed on May 7, 2001, now Pat. No. 6,975,898.

(60) Provisional application No. 60/212,411, filed on Jun. 19, 2000.

(51) Int. Cl.
*A61B 6/00* (2006.01)
(52) U.S. Cl. ............. 600/476; 600/407; 385/12; 385/43
(58) Field of Classification Search .................. 600/407, 600/476
See application file for complete search history.

(56) References Cited

U.S. PATENT DOCUMENTS

| | | | |
|---|---|---|---|
| 3,889,662 A | 6/1975 | Mitsui | 600/139 |
| 3,918,438 A | 11/1975 | Hayamizu et al. | 600/168 |
| 4,118,270 A | 10/1978 | Pan et al. | 156/659 |
| 4,234,788 A | 11/1980 | Palmer et al. | 250/227 |
| 4,265,699 A | 5/1981 | Ladany | 156/657 |

(Continued)

FOREIGN PATENT DOCUMENTS

| | | |
|---|---|---|
| DE | 4428967 | 12/1995 |
| EP | 0 713 672 | 5/1996 |

(Continued)

OTHER PUBLICATIONS

Barhoum et al., "Optical modeling of an ultrathin scanning fiber endoscope, a preliminary study of confocal versus non-confocal detection." Optics Express, vol. 13, No. 19: 7548-7562, Sep. 19, 2005.

(Continued)

*Primary Examiner* — Brian Casler
*Assistant Examiner* — Nasir S Shahrestani
(74) *Attorney, Agent, or Firm* — Wilson Sonsini Goodrich & Rosati

(57) ABSTRACT

An apparatus and method for providing image acquisition and/or image display in a limited region of interest (ROI). The apparatus comprises a micro-electro-mechanical system (MEMS), preferably integrating a light source, a cantilever, a lens, an actuator, a light detector, and a position sensor. The light source provides light for illuminating the ROI, displaying an image, providing a therapy, and/or performing other functions. The cantilever comprises a resin waveguide with a fixed end attached to a substrate that supports many or all other components. A free end of the cantilever is released from the substrate during fabrication and includes the lens. The actuator scans the free end in orthogonal directions to illuminate the ROI or display an image. The position sensors detect the position of the free end for control. The light detector receives light backscattered from the ROI separate from, or at the fixed end of the cantilever.

16 Claims, 12 Drawing Sheets

U.S. PATENT DOCUMENTS

| | | | | |
|---|---|---|---|---|
| 4,410,235 | A | 10/1983 | Klement et al. | 350/96.18 |
| 4,454,547 | A | 6/1984 | Yip et al. | 358/293 |
| 4,686,963 | A | 8/1987 | Cohen et al. | 128/4 |
| 4,688,555 | A | 8/1987 | Wardle | 128/4 |
| 4,695,163 | A | 9/1987 | Schachar | 356/369 |
| 4,710,619 | A | 12/1987 | Haberl | 250/203 |
| 4,743,283 | A | 5/1988 | Borsuk | 65/2 |
| 4,758,222 | A | 7/1988 | McCoy | 604/95 |
| 4,762,118 | A | 8/1988 | Lia et al. | 128/4 |
| 4,768,513 | A | 9/1988 | Suzuki | 128/634 |
| 4,782,228 | A | 11/1988 | Westell | 250/236 |
| 4,804,395 | A | 2/1989 | Clark et al. | 65/2 |
| 4,824,195 | A | 4/1989 | Khoe | 350/96.18 |
| 4,850,364 | A | 7/1989 | Leavitt | 128/661.09 |
| 4,928,316 | A | 5/1990 | Heritage et al. | 455/600 |
| 4,979,496 | A | 12/1990 | Komi | 128/4 |
| 4,983,165 | A | 1/1991 | Loiterman | 604/95 |
| 5,037,174 | A | 8/1991 | Thompson | 385/33 |
| 5,074,642 | A | 12/1991 | Hicks | 385/116 |
| 5,103,497 | A | 4/1992 | Hicks | 385/117 |
| 5,172,685 | A | 12/1992 | Nudelman | 128/6 |
| 5,209,117 | A | 5/1993 | Bennett | 73/517 |
| 5,231,286 | A | 7/1993 | Kajimura et al. | 250/234 |
| 5,247,174 | A | 9/1993 | Berman | 250/235 |
| 5,272,330 | A | 12/1993 | Betzig et al. | 250/216 |
| 5,286,970 | A | 2/1994 | Betzig et al. | 250/227.26 |
| 5,305,759 | A | 4/1994 | Kaneko et al. | 600/476 |
| 5,321,501 | A | 6/1994 | Swanson et al. | 356/345 |
| 5,360,968 | A | 11/1994 | Scott | 235/454 |
| 5,381,782 | A | 1/1995 | DeLaRama et al. | 128/4 |
| 5,394,500 | A | 2/1995 | Marchman | 385/123 |
| 5,405,337 | A | 4/1995 | Maynard | 604/281 |
| 5,425,123 | A | 6/1995 | Hicks | 385/117 |
| 5,459,803 | A | 10/1995 | Yamane et al. | 385/33 |
| 5,480,046 | A | 1/1996 | Filas et al. | 216/7 |
| 5,507,725 | A | 4/1996 | Savage et al. | 604/95 |
| 5,512,035 | A | 4/1996 | Konstorum et al. | 600/146 |
| 5,535,759 | A | 7/1996 | Wilk | 128/898 |
| 5,549,542 | A | 8/1996 | Kovalcheck | 600/146 |
| 5,563,969 | A | 10/1996 | Honmou | 385/35 |
| 5,570,441 | A | 10/1996 | Filas et al. | 385/43 |
| 5,621,830 | A | 4/1997 | Lucey et al. | 385/25 |
| 5,627,922 | A | 5/1997 | Kopelman et al. | 385/12 |
| 5,643,175 | A | 7/1997 | Adair | 600/133 |
| 5,649,897 | A | 7/1997 | Nakamura | 600/111 |
| 5,668,644 | A | 9/1997 | Kuroiwa et al. | 358/480 |
| 5,703,979 | A | 12/1997 | Filas et al. | 385/43 |
| 5,715,337 | A | 2/1998 | Spitzer et al. | 385/4 |
| 5,724,169 | A | 3/1998 | LaGasse | 359/173 |
| 5,727,098 | A | 3/1998 | Jacobson | 385/31 |
| 5,765,561 | A | 6/1998 | Chen et al. | 128/653.1 |
| 5,894,122 | A | 4/1999 | Tomita | 250/234 |
| 5,906,620 | A | 5/1999 | Nakao et al. | 606/113 |
| 5,919,200 | A | 7/1999 | Stambaugh et al. | 606/159 |
| 5,939,709 | A | 8/1999 | Ghislain et al. | 250/216 |
| 5,947,905 | A | 9/1999 | Hadjicostis et al. | 600/463 |
| 5,984,860 | A | 11/1999 | Shan | 600/116 |
| 5,991,697 | A | 11/1999 | Nelson et al. | 702/49 |
| 6,035,229 | A | 3/2000 | Silverstein et al. | 600/473 |
| 6,046,720 | A | 4/2000 | Melville et al. | 345/108 |
| 6,059,719 | A | 5/2000 | Yamamoto et al. | 600/127 |
| 6,069,698 | A | 5/2000 | Ozawa et al. | 356/345 |
| 6,081,605 | A | 6/2000 | Roth et al. | 382/103 |
| 6,091,067 | A | 7/2000 | Drobot et al. | 250/234 |
| 6,096,054 | A | 8/2000 | Wyzgala et al. | 606/170 |
| 6,097,528 | A | 8/2000 | Lebby et al. | 359/251 |
| 6,134,003 | A | 10/2000 | Tearney et al. | 356/345 |
| 6,142,957 | A | 11/2000 | Diamond et al. | 600/600 |
| 6,148,095 | A | 11/2000 | Prause et al. | 382/131 |
| 6,161,035 | A | 12/2000 | Furusawa | 600/476 |
| 6,169,281 | B1 | 1/2001 | Chen et al. | 250/234 |
| 6,185,443 | B1 | 2/2001 | Crowley | 600/407 |
| 6,191,862 | B1 | 2/2001 | Swanson et al. | 356/450 |
| 6,211,904 | B1 | 4/2001 | Adair et al. | 348/76 |
| 6,215,437 | B1 | 4/2001 | Schurmann et al. | 342/42 |
| 6,240,312 | B1 | 5/2001 | Alfano et al. | 600/476 |
| 6,241,657 | B1 | 6/2001 | Chen et al. | 600/117 |
| 6,246,914 | B1 | 6/2001 | de la Rama et al. | 607/122 |
| 6,289,144 | B1 | 9/2001 | Neuschafer et al. | 385/12 |
| 6,294,775 | B1 | 9/2001 | Seibel et al. | 250/208.1 |
| 6,327,493 | B1 | 12/2001 | Ozawa et al. | 600/476 |
| 6,370,422 | B1 | 4/2002 | Richards-Kortum et al. | 600/478 |
| 6,387,119 | B2 | 5/2002 | Wolf et al. | 623/1.11 |
| 6,388,641 | B2 | 5/2002 | Tidwell et al. | 345/32 |
| 6,441,359 | B1 | 8/2002 | Cozier et al. | 250/216 |
| 6,443,894 | B1 | 9/2002 | Sumanaweera et al. | 600/443 |
| 6,461,337 | B1 | 10/2002 | Minotti et al. | 604/264 |
| 6,466,687 | B1 | 10/2002 | Uppaluri et al. | 382/128 |
| 6,485,413 | B1 * | 11/2002 | Boppart et al. | 600/160 |
| 6,492,962 | B2 | 12/2002 | Melville et al. | 345/32 |
| 6,515,274 | B1 | 2/2003 | Moskovits et al. | 250/216 |
| 6,515,781 | B2 | 2/2003 | Lewis et al. | 359/204 |
| 6,525,310 | B2 | 2/2003 | Dunfield | 250/235 |
| 6,545,260 | B1 | 4/2003 | Ono et al. | 250/227.26 |
| 6,546,271 | B1 | 4/2003 | Reisfeld | 600/407 |
| 6,549,801 | B1 | 4/2003 | Chen et al. | 600/425 |
| 6,550,918 | B1 | 4/2003 | Agostinelli et al. | 353/7 |
| 6,563,105 | B2 | 5/2003 | Seibel et al. | 250/208.1 |
| 6,563,998 | B1 * | 5/2003 | Farah et al. | 385/131 |
| 6,564,087 | B1 | 5/2003 | Pitris et al. | 600/478 |
| 6,564,089 | B2 | 5/2003 | Izatt et al. | 600/478 |
| 6,567,678 | B1 | 5/2003 | Oosta et al. | 600/316 |
| 6,612,980 | B2 | 9/2003 | Chen et al. | 600/117 |
| 6,615,072 | B1 | 9/2003 | Izatt et al. | 600/478 |
| 6,678,541 | B1 | 1/2004 | Durkin et al. | 600/310 |
| 6,685,718 | B1 | 2/2004 | Wyzgala et al. | 606/170 |
| 6,687,010 | B1 | 2/2004 | Horii et al. | 356/479 |
| 6,689,064 | B2 | 2/2004 | Hager et al. | 600/454 |
| 6,690,963 | B2 | 2/2004 | Ben-Haim et al. | 600/424 |
| 6,694,983 | B2 | 2/2004 | Wolf et al. | 128/898 |
| 6,735,463 | B2 | 5/2004 | Izatt et al. | 600/476 |
| 6,755,532 | B1 | 6/2004 | Cobb | 353/7 |
| 6,773,394 | B2 | 8/2004 | Taniguchi et al. | 600/117 |
| 6,779,892 | B2 | 8/2004 | Agostinelli et al. | 353/7 |
| 6,785,571 | B2 | 8/2004 | Glossop | 600/424 |
| 6,788,967 | B2 | 9/2004 | Ben-Haim et al. | 600/424 |
| 6,818,001 | B2 | 11/2004 | Wulfman et al. | 606/159 |
| 6,826,342 | B1 | 11/2004 | Bise et al. | 385/125 |
| 6,832,984 | B2 | 12/2004 | Stelzer et al. | 604/93.01 |
| 6,836,560 | B2 | 12/2004 | Emery | 382/145 |
| 6,839,586 | B2 | 1/2005 | Webb | 600/478 |
| 6,845,190 | B1 | 1/2005 | Smithwick et al. | 385/25 |
| 6,856,712 | B2 | 2/2005 | Fauver et al. | 385/12 |
| 6,858,005 | B2 | 2/2005 | Ohline et al. | 600/141 |
| 6,872,433 | B2 | 3/2005 | Seward et al. | 428/36.9 |
| 6,882,429 | B1 | 4/2005 | Weitekamp et al. | 356/482 |
| 6,889,175 | B2 | 5/2005 | Green | 702/190 |
| 6,892,090 | B2 | 5/2005 | Verard et al. | 600/424 |
| 6,895,270 | B2 | 5/2005 | Ostrovsky | 600/476 |
| 6,902,528 | B1 | 6/2005 | Garibaldi et al. | 600/118 |
| 6,932,829 | B2 | 8/2005 | Majercak | 606/198 |
| 6,975,898 | B2 | 12/2005 | Seibel et al. | 600/473 |
| 7,004,173 | B2 | 2/2006 | Sparks et al. | 128/898 |
| 7,023,558 | B2 | 4/2006 | Fee et al. | 356/489 |
| 7,038,191 | B2 | 5/2006 | Kare et al. | 250/227.11 |
| 7,072,046 | B2 | 7/2006 | Xie et al. | 356/479 |
| 7,158,234 | B2 | 1/2007 | Uchiyama et al. | 356/479 |
| 7,170,610 | B2 | 1/2007 | Knuttel | 356/456 |
| 7,179,220 | B2 | 2/2007 | Kukuk | 600/118 |
| 7,189,961 | B2 | 3/2007 | Johnston et al. | 250/234 |
| 7,230,583 | B2 | 6/2007 | Tidwell et al. | 345/8 |
| 7,252,674 | B2 | 8/2007 | Wyzgala et al. | 606/170 |
| 7,261,687 | B2 | 8/2007 | Yang | 600/173 |
| 7,324,211 | B2 | 1/2008 | Tsujita | 356/497 |
| 7,349,098 | B2 | 3/2008 | Li et al. | 356/479 |
| 7,366,376 | B2 | 4/2008 | Shishkov et al. | 385/35 |
| 7,404,929 | B2 | 7/2008 | Fulghum, Jr. | 422/82.05 |
| 7,447,408 | B2 | 11/2008 | Bouma et al. | 385/123 |
| 7,473,232 | B2 | 1/2009 | Teague | 600/567 |
| 7,515,274 | B2 | 4/2009 | Gelikonov et al. | 356/479 |
| 7,530,948 | B2 | 5/2009 | Seibel et al. | 600/102 |
| 7,615,005 | B2 | 11/2009 | Stefanchik et al. | 600/106 |
| 7,616,986 | B2 | 11/2009 | Seibel et al. | 600/476 |
| 7,747,312 | B2 | 6/2010 | Barrick et al. | 600/426 |
| 7,783,337 | B2 | 8/2010 | Feldman et al. | 600/160 |
| 7,901,348 | B2 | 3/2011 | Soper et al. | 600/117 |

| | | | |
|---|---|---|---|
| 2001/0030744 A1 | 10/2001 | Chang et al. ............... 356/73 |
| 2002/0071625 A1 | 6/2002 | Bartholomew et al. ......... 385/12 |
| 2003/0009189 A1 | 1/2003 | Gilson et al. ............... 606/200 |
| 2003/0032878 A1 | 2/2003 | Shahidi ..................... 600/429 |
| 2003/0045778 A1 | 3/2003 | Ohline et al. ............... 600/114 |
| 2003/0055317 A1 | 3/2003 | Taniguchi et al. ........... 600/117 |
| 2003/0103199 A1 | 6/2003 | Jung et al. ................... 356/73 |
| 2003/0103665 A1 | 6/2003 | Uppaluri et al. ............ 382/131 |
| 2003/0142934 A1 | 7/2003 | Pan et al. ................... 385/116 |
| 2003/0160721 A1 | 8/2003 | Gilboa et al. ............... 342/450 |
| 2003/0179428 A1 | 9/2003 | Suzuki et al. ............... 359/204 |
| 2003/0208107 A1 | 11/2003 | Refael ....................... 600/300 |
| 2003/0208134 A1 | 11/2003 | Secrest et al. .............. 600/562 |
| 2003/0216639 A1 | 11/2003 | Gilboa et al. ............... 600/424 |
| 2003/0220749 A1 | 11/2003 | Chen et al. .................. 702/31 |
| 2003/0236564 A1 | 12/2003 | Majercak .................... 623/1.11 |
| 2004/0015049 A1 | 1/2004 | Zaar .......................... 600/101 |
| 2004/0015053 A1 | 1/2004 | Bieger et al. ................ 600/117 |
| 2004/0033006 A1 | 2/2004 | Farah .......................... 385/14 |
| 2004/0061072 A1 | 4/2004 | Gu et al. .................... 250/458.1 |
| 2004/0118415 A1 | 6/2004 | Hall et al. .................. 128/898 |
| 2004/0147827 A1 | 7/2004 | Bowe ......................... 600/374 |
| 2004/0176683 A1 | 9/2004 | Whitin et al. ............... 600/424 |
| 2004/0181148 A1 | 9/2004 | Uchiyama et al. .......... 600/425 |
| 2004/0199052 A1 | 10/2004 | Banik et al. ................ 600/142 |
| 2004/0243227 A1 | 12/2004 | Starksen et al. ........... 623/2.11 |
| 2004/0249267 A1 | 12/2004 | Gilboa ....................... 600/204 |
| 2004/0260199 A1 | 12/2004 | Hardia et al. ............... 600/566 |
| 2005/0020878 A1 | 1/2005 | Ohnishi et al. ............. 600/117 |
| 2005/0020926 A1 | 1/2005 | Wiklof et al. .............. 600/476 |
| 2005/0036150 A1 | 2/2005 | Izatt et al. ................... 356/479 |
| 2005/0054931 A1 | 3/2005 | Clark ......................... 600/453 |
| 2005/0065433 A1 | 3/2005 | Anderson .................. 600/424 |
| 2005/0085693 A1 | 4/2005 | Belson et al. ............... 600/146 |
| 2005/0111009 A1 | 5/2005 | Keightley et al. .......... 356/602 |
| 2005/0168751 A1 | 8/2005 | Horii et al. ................. 356/479 |
| 2005/0171438 A1 | 8/2005 | Chen et al. .................. 600/476 |
| 2005/0171592 A1 | 8/2005 | Majercak .................... 623/1.11 |
| 2005/0183733 A1 | 8/2005 | Kawano et al. ............. 128/899 |
| 2005/0206774 A1 | 9/2005 | Tsujimoto .................. 348/345 |
| 2005/0215854 A1 | 9/2005 | Ozaki et al. ................ 600/109 |
| 2005/0215911 A1 | 9/2005 | Alfano et al. .............. 600/476 |
| 2005/0228290 A1 | 10/2005 | Borovsky et al. ........... 600/466 |
| 2005/0250983 A1 | 11/2005 | Tremaglio et al. .......... 600/101 |
| 2005/0272975 A1 | 12/2005 | McWeeney et al. ......... 600/113 |
| 2006/0015126 A1 | 1/2006 | Sher ........................... 606/159 |
| 2006/0030753 A1 | 2/2006 | Boutillette et al. .......... 600/146 |
| 2006/0052662 A1 | 3/2006 | Kress .......................... 600/123 |
| 2006/0100480 A1 | 5/2006 | Ewers et al. ............... 600/114 |
| 2006/0126064 A1 | 6/2006 | Bambot et al. .............. 356/337 |
| 2006/0149134 A1 | 7/2006 | Soper et al. ................ 600/182 |
| 2006/0149163 A1 | 7/2006 | Hibner et al. ............... 600/566 |
| 2006/0187462 A1 | 8/2006 | Srinivasan et al. .......... 356/479 |
| 2006/0202115 A1 | 9/2006 | Lizotte et al. .............. 250/234 |
| 2006/0252993 A1 | 11/2006 | Freed et al. ................. 600/146 |
| 2007/0038119 A1 | 2/2007 | Chen et al. .................. 600/476 |
| 2007/0066983 A1 | 3/2007 | Maschke .................... 606/159 |
| 2007/0088219 A1 | 4/2007 | Xie et al. .................... 600/473 |
| 2007/0093703 A1 | 4/2007 | Sievert et al. .............. 600/343 |
| 2007/0129601 A1 | 6/2007 | Johnston et al. ............ 600/109 |
| 2007/0213618 A1 | 9/2007 | Li et al. ...................... 600/476 |
| 2007/0270650 A1 | 11/2007 | Eno et al. ................... 600/145 |
| 2008/0004491 A1 | 1/2008 | Karasawa .................... 600/101 |
| 2008/0221388 A1 | 9/2008 | Seibel et al. ................ 600/109 |

FOREIGN PATENT DOCUMENTS

| | | |
|---|---|---|
| EP | 0 520 388 | 9/1996 |
| EP | 1 077 360 | 2/2001 |
| EP | 1 088 515 | 4/2001 |
| EP | 1 142 529 | 10/2001 |
| EP | 0 712 032 | 12/2001 |
| EP | 1 310 206 | 5/2003 |
| EP | 1 421 913 | 5/2004 |
| EP | 0 910 284 | 1/2007 |
| EP | 1 063 921 | 2/2007 |
| JP | 05-154154 | 6/1993 |
| JP | 06-511312 | 12/1994 |
| JP | 2001174744 | 6/2001 |
| WO | WO 93/20742 | 10/1993 |
| WO | WO 96/02184 | 2/1996 |
| WO | WO 98/38907 | 9/1998 |
| WO | WO 98/43530 | 10/1998 |
| WO | WO 99/04301 | 1/1999 |
| WO | WO 01/97902 | 12/2001 |
| WO | WO 2005/024496 | 3/2005 |

OTHER PUBLICATIONS

Barnard et al., "Mode Transforming Properties of Tapered Single-mode Fiber Microlens." *Appl. Opt.* vol. 32, No. 12: 2090-2094, Apr. 20, 1993.

Barnard et al., "Single-mode Fiber Microlens with Controllable Spot Size." *Appl. Opt.* vol. 30, No. 15: 1958-1962, May 20, 1991.

Bird et al., "Two-photon fluorescence endoscopy with a micro-optic scanning head." *Optics Letters*, vol. 28, No. 17: 1552-1554, 2003.

Borreman et al., "Fabrication of Polymeric Multimode Waveguides and Devices in SU-8 Photoresist Using Selective Polymerization." *Proceedings Symposium IEEE/LEOS Benelux Chapter, Amsterdam:* pp. 83-86, 2002.

Brown et al., "Recognising Panoramas." *Proceedings of the Ninth IEEE International Conference on Computer Vision* 8pp., Apr. 2003.

Brunetaud et al., "Lasers in Digestive Endoscopy." *Journal of Biomedical Optics* vol. 2, No. 1: 42-52, Jan. 1997.

Chen et al., "Dispersion management up to the third order for real-time optical coherence tomography involving a phase or frequency modulator." *Optics Express* vol. 12, No. 24: 5968-5978, 2004.

Chen et al., "Optical Doppler tomographic imaging of fluid flow velocity in highly scattering media." *Optics Letters*, vol. 22, No. 1: 64-66, 1997.

Clark et al., "Fiber delivery of femtosecond pulses from a Ti:sapphire laser." *Optics Letters*, vol. 26, No. 17: 1320-1322, 2001.

Deschamps et al., "Automatic construction of minimal paths in 3D images: An application to virtual endoscopy." *CARS'99* —H. U Lemke, M.W. Vannier, K. Inamura & A.G. Fannan (Editors) *Elsevier Science B.V.*: 151-155, 1999.

Dickensheets et al., "A Scanned Optical Fiber Confocal Microscope." *Three-Dimensional Microscopy* SPIE vol. 2184: 39-47, 1994.

Dickensheets et al., "Micromachined scanning confocal optical microscope." *Optics Letters*, vol. 21, No. 10: 764-766, May 15, 1996.

Drexler et al., "In vivo ultrahigh-resolution optical coherence tomography." *Optics Letters*, vol. 24, No. 17: 1221-1223, 1999.

Finci et al., "Tandem balloon catheter for coronary angioplasty." *Catheter Cardiovascular Diagnosis* vol. 12, No. 6: 421-425, 1986. 2pp Abstract.

Flusberg et al., "In vivo brain imaging using a portable 3.9 gram two-photon fluorescence microendoscope." *Optics Letters*, vol. 30, No. 17: 2272-2274. 2005.

Fu et al., "Nonlinear optical microscopy based on double-clad photonic crystal fibers." *Optics Express* vol. 13, No. 14: 5528-5534 + supplemental page, 2005.

Göbel et al., "Miniaturized two-photon microscope based on a flexible coherent fiber bundle and a gradient-index lens objective." *Optics Letters*, vol. 29, No. 21: 2521-2523, 2004.

Helmchen et al., "A Miniature Head-Mounted Two-Photon Microscope: High Resolution Brain Imaging in Freely Moving Animals." *NEURON* vol. 31: 903-912, Sep. 27, 2001.

Herline et al., "Surface Registration for Use in Interactive, Image-Guided Liver Surgery." *Computer Aided Surgery*, vol. 5: 11-17, 1999.

Higgins et al., "Integrated Bronchoscopic Video Tracking and 3D CT Registration for Virtual Bronchoscopy." *Medical Imaging 2003*, vol. 5031: 80-89, 2003.

Huang et al., "Optical Coherence Tomography." *Science* vol. 254, Issue 5035: 1178-1181, 1991.

Huber et al., "Amplified, frequency swept lasers for frequency domain reflectometry and OCT imaging: design and scaling principles." *Optics Express* vol. 13, No. 9: 3513-3528, May 2, 2005.

Jung et al., "Multiphoton endoscopy." *Optics Letters*, vol. 28, No. 11: 902-904, 2003.

Kiesslich et al., "Diagnosing *Helicobacter pylori* In Vivo by Confocal Laser Endoscopy." *Gastroenterology* vol. 128: 2119-2123, 2005.

Kiraly et al., "Three-Dimensional Path Planning for Virtual Bronchoscopy." *IEEE Transactions on Medical Imaging*, vol. 23, No. 9: 1365-1379, Sep. 2004.

Lee et al., "Microlenses on the End of Single-mode Optical Fibers for Laser Applications." *Appl. Opt.* vol. 24, No. 19: 3134-3139, Oct. 1, 1985.

Lewis et al., "Scanned beam medical imager." *MOEMS Display and Imaging System II*, edited by Hakan Urey, David L. Dickensheets, Proceedings of SPIE, Bellingham, WA, vol. 5348: 40-51, 2004.

Lexer et al., "Dynamic coherent focus OCT with depth-independent transversal resolution." *Journal of Modern Optics* vol. 46, No. 3: 541-553, 1999.

Li et al., "Optical Coherence Tomography: Advanced Technology for the Endoscopic Imaging of Barrett's Esophagus" *Endoscopy*, vol. 32, No. 12: 921-930, 2000.

Liu et al., "3D Navigation for Endoscope by Magnetic Field." *Proceedings of SPIE*, vol. 4556 25-28, 2001.

Liu et al., "Rapid-scanning forward-imaging miniature endoscope for real-time optical coherence tomography." *Optics Letters*, vol. 29, No. 15: 1763-1765, 2004.

Martinez, O.E., "3000 Times Grating Compressor with Positive Group-Velocity Dispersion—Application to Fiber Compensation in 1.3-1.6 µm Region."*IEEE Journal of Quantum Electronics* vol. 23: 59-64, 1987.

Mori et al., "A Method for Tracking camera motion of real endoscope by using virtual endoscopy system," *Proceedings of SPIE*: 1-12, 2000. <www.http://www.toriwaki.nuie.nagoya-u.ac.jp> 12pp 1-12.

Morofke et al., "Wide dynamic range detection of bidirectional flow in Doppler Optical coherence tomograph using a two-dimensional Kasai estimator," *Optics Letters*, vol. 32, No. 3: 253-255, Feb. 1, 2007.

Murakami et al., "A Miniature Confocal Optical Microscope With Mems Gimbl scanner."*The 12th International Conference on Solid Sate Sensors, Actuators and Microsystems* Boston: 587-590, Jun. 8-12, 2003.

Myaing et al., "Enhanced two-photon biosensing with double-clad photonic crystal fibers," *Optics Letters*, vol. 28, No. 14: 1224-1226, 2003.

Ohmi et al., "Quasi In-Focus Optical Coherence Tomography." *Japanese Journal of Applied Physics* vol. 43, No. 2: 845-849, 2004.

Oikawa et al., "Intra-operative Guidance with Real-time Information of Open MRI and Manipulators Using Coordinate-Integration Module." *Proceedings of SPIE*, vol. 5029: 653-600, 2003.

Pagoulatos et al., "Image-based Registration of Ultrasound and Magnetic Resonance Images: A Preliminary Study,"*Proceedings of SPIE*, vol. 3976: 156-164, 2000.

Patterson et al., "Applications of time-resolved light scattering measurements to photodynamic therapy dosimetry,"*SPIE* vol. 1203, Photodynamic Therapy: Mechanism II: 62-75, 1990.

Pyhtila et al., "Determining nuclear morphology using an improved angle-resolved low coherence interferometry system." *Optics Express*, vol. 11, No. 25: 3473-3484, Dec. 15, 2003.

Pyhtila et al., "Fourier-domain angle-resolved low coherence interferometry through an endoscopic fiber bundle for light-scattering spectroscopy." *Optics Letters*, vol. 31, No. 6: 772-774, Dec. 1, 2005.

Pyhtila et al., "Rapid, depth-resolved light scattering measurements using Fourier domain, angle-resolved low coherence interferometry." *Optical Society of America*: 6pp, 2004.

Podoleanu et al., "Three dimensional OCT images from retina and skin." *Optics Express* vol. 7, No. 9: 292-298, 2000.

Qi et al., "Dynamic focus control in high-speed optical coherence tomography based on a microelectromechanical mirror." *Optics Communications* vol. 232: 123-128, 2004.

Russo et al., "Lens-ended Fibers for Medical Applications: A New Fabrication Technique." *Appl. Opt.* vol. 23, No. 19: 3277-3283, Oct. 1, 1984.

Sasaki et al., "Scanning Near-Field Optical Microscope using Cantilever Integrated with Light Emitting Diode, Waveguide, Aperture, and Photodiode." Optical MEMS 2000 Invited Speakers: Advance Program, Sponsored by IEEE Lasers and Electro-Optics Society: 16pp, 2000. Available at <http://www.ieee.org/organizations/society/leos/LEOSCONF/MEMS/omspeak.html.>.

Schmitt et al., "An optical coherence microscope with enhanced resolving power in thick tissue." *Optics Communications* 142: 203-207, 1997.

Schwartz et al., "Electromagnetic Navigation during Flexible Bronchoscopy." *Interventional Pulmonology: Respiration*, vol. 70: 516-522, 2003.

Seibel et al., "Unique Features of Optical Scanning, Single Fiber Endoscopy." *Lasers in Surgery and Medicine* vol. 30: 177-183, 2002.

Shahidi et al., "Implementation, Calibration and Accuracy Testing of an Image-Enhanced Endoscopy System." *IEEE Transactions On Medical Imaging*, vol. 21, No. 12: 1524-1535, 2002.

Shinagawa et al., "CT-Guided Transbronchial Biopsy Using an Ultrathin Bronchoscopic Navigation." *Chest*, vol. 125, No. 3: 1138-1143, 2003.

Shiraishi et al., "Spot Size Reducer for Standard Single-Mode Fibers Utilizing a Graded-Index Fiber Tip." *ECOC 97:* 50-53, Sep. 22-25, 1997.

Shoji et al., "Camera motion tracking of real endoscope by using virtual endoscopy system and texture information." *Proceedings of SPIE*, vol. 4321: 122-133, 2001.

Skala et al., "Multiphoton Microscopy of Endogenous Fluorescence Differentiates Normal, Precancerous, and Cancerous Squamous Epithelial Tissues." *Cancer Research* vol. 65, No. 4: 1180-1186, Feb. 15, 2005. Available at <www.aacrjournals.org>.

Smithwick et al., "Modeling and Control of the Resonant Fiber Scanner for Laser Scanning Display or Acquisition." *SID 03 DIGEST:* 1455-1457, 2003.

Solomon et al., "Three-dimensional CT-Guided Bronchoscopy With a Real-Time Electromagnetic Position Sensor," "A Comparison of Two Image Registration Methods." *Chest*, vol. 118, No. 6: 1783-1787, 2000.

Srivastava, S., "Computer-Aided Identification of Ovarian Cancer in Confocal Microendoscope Images," Department of Electrical and Computer Engineering, University of Arizona Graduate School, Thesis: 213pp, 2004.

Tearney et al., "Determination of the Refractive-Index of Highly Scattering Human Tissue by Optical Coherence Tomography." *Optics Letters*, vol. 20, No. 21: 2258-2260, 1995.

Tsai et al., "All-Optical Histology Using Ultrashort Laser Pulses." *Neuron* Cell Press, vol. 39: 27-41, Jul. 3, 2003.

Vakoc et al., "Comprehensive esophageal microscopy by using optical frequency-domain imaging (with video)." *Gastrointestinal Endoscopy*, vol. 65, No. 6: 898-905, 2007.

Wang et al., "Deep Reactive Ion Etching of Silicon Using an Aluminum Etching Mask." *Proceedings of SPIE*, vol. 4876: 633-640, 2003.

Wilson et al., "Optical Reflectance and Transmittance of Tissues: Principles and Applications." *IEEE Journal of Quantum Electronics*, vol. 26, No. 12: 2186-2199, Dec. 1990.

Xu et al., "3D Motion Tracking of pulmonary lesions using CT fluoroscopy images for robotically assisted lung biopsy." *Proceedings of SPIE*, vol. 5367: 394-402, 2004.

Yamada et al., "Characteristics of a Hemispherical Microlens for Coupling Between a Semiconductor Laser and Single-Mode Fiber." *IEEE J. Quant. Electron*, vol. QE-16, No. 10: 1067-1072, Oct. 1980.

Yamamoto et al., "Total enteroscopy with a nonsurgical steerable double-balloon method." *Gastrointestinal Endoscopy* vol. 53, No. 2: 216-220, Feb. 2001. Abstract only.

Yang et al., "High speed, wide velocity dynamic range Doppler optical coherence tomography (Part I): System design, signal processing, and performance." *Optics Express*, vol. 11, No. 7: 794-809, Apr. 7, 2003.

Yang et al., "Micromachined array tip for multifocus fiber-based optical coherence tomography." *Optics Letters*, vol. 29, No. 15: 1754-1756, 2004.

Yelin et al., "Double-clad fiber for endoscopy." *Optics Letters*, vol. 29, No. 20: 2408-2410, Oct. 15, 2004.

Yelin et al., "Three-dimensional miniature endoscopy." *Nature* vol. 443: 765 plus supplemental information, Oct. 19, 2006. <www.nature.com/nature/journal/v443/n7113/extref/443765a-s2.doc>.

Yoon et al., "Analysis of Electro Active Polymer Bending: A Component in a Low Cost Ultrathin Scanning Endoscope." *Sensors and Actuators A—Physical*: pp. 1-26, Submitted Jan. 13, 2006, Published Jul. 2006.

Yun et al., "Comprehensive volumetric optical microscopy in vivo." *Nature Medicine* vol. 12, No. 12: 1429-1433, Dec. 2006.

Yun et al., "Motion artifacts in optical coherence tomography with frequency-domain ranging." *Optics Express* vol. 12, No. 13: 2977-2998, Jun. 28, 2004.

Zhang et al., "In vivo blood flow imaging by a swept laser source based Fourier domain optical Doppler tomography." *Optics Express* vol. 13, No. 19: 7449-7457, Sep. 19, 2005.

Zipfel et al., "Live tissue intrinsic emission microscopy using multiphoton-excited native fluorescence and second harmonic generation." *PNAS* vol. 100, No. 12: 7075-7080, Jun. 10, 2003. Available at <www.pnas.org/cgi/doi/10.1073/pnas.0832308100>.

n. a., "Given® Diagnostic System." The Platform for PillCam™ Endoscopy Given Imaging Ltd.: 4pp, 2001-2004. <http:www.givenimaging.com>.

n. a., "NASA-Inspired Shape-Sensing Fibers Enable Minimally Invasive Surgery." NASA Tech Briefs vol. 32, No. 2: 12, 14, Feb. 2008.

n. a., "NANO™SU-8 2000 Negative Tone Photoresist Formulations 2002-2025." Micro-Chem: 5pp, © 2001.

\* cited by examiner

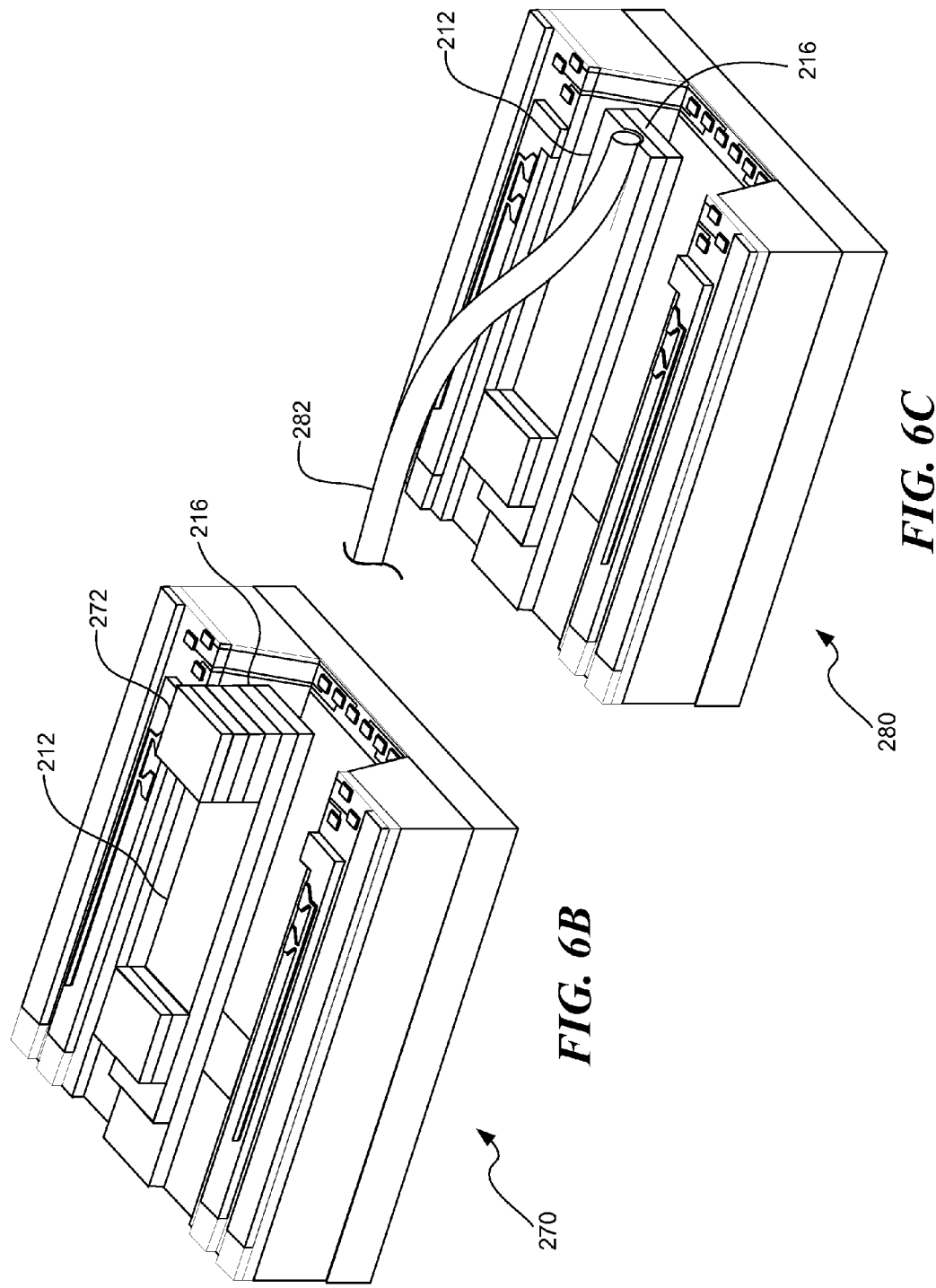

INTEGRATED OPTICAL SCANNING IMAGE ACQUISITION AND DISPLAY

RELATED APPLICATIONS

This application is a continuation of a copending patent application Ser. No. 10/655,482, filed on Sep. 4, 2003, which itself is a continuation-in-part of prior patent application Ser. No. 09/850,594, filed on May 7, 2001, and now issued on Dec. 13, 2005, as U.S. Pat. No. 6,975,898, the benefit of the filing date of which is hereby claimed under 35 U.S.C. §120. Application Ser. No. 09/850,594 is itself based on a prior copending provisional application Ser. No. 60/212,411, filed on Jun. 19, 2000, the benefit of the filing date of which is hereby claimed under 35 U.S.C. §119(e).

GOVERNMENT RIGHTS

This invention was made with government support under grant numbers CA094303 and CA096633 awarded by the National Institutes of Health. The government has certain rights in this invention.

FIELD OF THE INVENTION

The present invention generally relates to a micro-electromechanical system (MEMS) that conveys light to and from a region of interest (ROI), and more specifically, to a system that is selectively used for both imaging the ROI, and for displaying an image in the ROI.

BACKGROUND

Conventional small-scale image acquisition systems, such as endoscopes and boroscopes, typically sample an image plane using a bundle of optical fibers that correspond to pixels on a camera detector such as a charge coupled device (CCD). Trying to minimize a system's size using this approach is limited by a number of factors, including the overall diameter of the fiber bundle, the number of pixel detectors on the camera detector, and diffractive properties of light beams. Reducing the diameter of a conventional acquisition device reduces the possible number of pixels, and thus reduces the resolution and/or field of view (FOV) of the device. However, a reduction in diameter and size would enable users to examine areas unreachable by currently designed endoscopes, reduce collateral damage to tissue, and enable integration of imaging with other functional devices such as therapy devices.

Similarly, many small-scale image display systems, such as head mounted displays (HMDs), beam light from an optical fiber onto deflectable mirrors or rotating polygonal mirrors to produce an image on an image plane. This approach also has many size limitations. For instance, light beams of less than 3 millimeters (mm) are impractical for displays using mirrors, because mirror scanners and grating deflectors must be significantly larger than the light beam diameter to avoid clipping the beam or adding diffraction. Reducing the diameter of a conventional display device reduces the possible number of pixels, and thus reduces the resolution and/or field of view (FOV) of the device. However, a reduction in diameter and size would enable construction of more comfortable HMDs, and enable integration of display with other functional devices.

An older type of scanning image display system includes an electromechanical modulator. The modulator comprises a full width array of closely spaced fiber-like reflectors which deflect when a voltage potential is applied. The voltage potential is selectively applied to the reflector in accordance with an image signal. This technique requires a very complicated circuit to control the overall deflection of the reflectors and the overall size is quite large.

As one practical application, minimally invasive medical procedures (MIMPs) has increased the demand for small diameter systems that result in less tissue damage and trauma, faster recovery times, and lower risks to the patient. Typically, instruments used by practitioners of MIMPs include several different discrete systems for optical imaging, monitoring, maneuvering, sizing, diagnosis, biopsy, therapy, surgery, and non-visual monitoring/sensing. It would be preferable to combine the functions provided by these instruments in a single compact device to reduce the number of surgical ports that are currently required for a plurality of single-function tools. By employing an integrated multi-functional tool so that only one small port is used, the risks associated with repeatedly removing and inserting surgical tools can be dramatically reduced. Since most MIMPs require the practitioner to constantly monitor the procedure visually, optical imaging is considered a requirement for any fully integrated system for MIMPs. Thus, an appropriate multifunction instrument will most likely include an optical imaging system, and the imaging system should be compact so that it can be integrated with one or more diagnostic, and/or therapeutic tools.

The current tools used for MIMPs cannot readily be integrated with an optical imaging system without increasing the size of the resultant instrument to an excessive degree. All currently available commercial optical imaging systems that include a maneuverable flexible shaft must maintain a certain size (diameter) in order to preserve image quality. As indicated above, currently available flexible scopes cannot be made smaller than this limit unless image field-of-view (FOV) or resolution is sacrificed. Also, currently available imaging systems typically use an external light source to generate light, and use an optical waveguide to direct the light to an ROI within a patient's body. Although imaging and some diagnostic capability can be integrated into existing scopes, such as standard tissue imaging in combination with fluorescence for early detection of cancers, the optical systems of current flexible scopes are not sufficiently small to provide integrated diagnoses and therapies at the required degrees of performance, size, and price that will be demanded in the future by medical practitioners.

Presently available flexible scope designs use either a bundle of optical fibers (optical waveguides) and/or one or more cameras having an array of detectors to capture an image. Thus, the diameter of these flexible scopes employed for remote imaging cannot be reduced to smaller than the image size. Even if one ignores additional optical fibers used for illumination of an ROI, the scope diameter is therefore limited by the individual pixel size of a camera or by the diameter of optical fibers used to acquire the image. Currently, the smallest pixel element is determined by the size of the end of an optical fiber, which has a minimum core diameter of about 4 μm. To propagate light through an optical fiber, a surrounding cladding layer is required, increasing the minimum pixel size to more than 5 μm in diameter. If a standard video graphics adapter (sVGA) image is desired (e.g., with a resolution of 640×480 pixels), then a minimum diameter required for just the imaging optical fiber is more than 3 mm. Therefore, to achieve scopes with less than 3 mm overall diameter using current technologies, resolution and/or FOV must be sacrificed by having fewer pixel elements. All commercially available scopes suffer from this fundamental tradeoff between high image quality and small size.

Currently available scopes also suffer from poor control mechanisms. Some optical systems use an optical fiber and camera at a tip of a flexible scope to illuminate a ROI and acquire an image. The fiber and camera are manually controlled by the practitioner positioning the tip of the flexible scope. Other optical systems use a resonant fiber that is actuated into resonance with one or more nodes to produce a desired illumination spot. Although these systems actuate the fiber, such systems can not precisely control the position of the fiber tip without adding material to the fiber scan system and increasing the diameter and/or rigid-tip length. Other optical systems deflect or move mirrors to position the light beam rather than move the waveguide. However, as discussed above, mirrors must be larger than the light beam diameter to avoid clipping the beam or adding diffraction. Thus, the mirrors must be larger than the waveguide, thereby increasing the overall size of the instrument.

Some microscopes actuate a cantilever waveguide for near-field imaging. However, near-field systems have a very limited FOV (e.g., typically less than 500 nanometers), and a light-emitting tip must be positioned within nanometers of the target. Near-field systems are based on emitting light through a microscopic aperture with dimensions smaller than the wavelength of visible light. The emitted light reflects off the closely positioned target and is detected before the light has time to diffract and dissipate. A near-field system may be useful for imaging individual cells or molecules, but is not suitable for most medical procedures and other dynamic applications which require a FOV of at least a micron and can not be dependant on precisely positioning a tip within nanometers of the target. Using larger wavelengths to provide a suitable FOV with a near-field system would still require a substantially larger imaging system, which could not be integrated into a multi-function instrument. As an alternative, some microscopes actuate a cantilever waveguide for confocal microscope imaging. However, simple confocal systems are limited to single wavelength operation, which does not enable color imaging or display.

Thus, it would be desirable to reduce the imaging system for the purpose of reducing the overall size of an instrument used for MIMPs and other applications. To currently perform diagnostic or therapeutic MIMPs, one or more separate instruments are used within the FOV of a standard endoscopic imager, and any additional separate instrument must often be held and maneuvered by a second medical practitioner. Typically, the second instrument provides a high intensity point source of light for optical therapies, a hot-tipped probe for thermal therapies, or a trocar used for mechanical cutting. The second instrument is moved to the surface of the tissue and usually moved within or across the surface of the tissue, covering the area of interest as the tool is scanned and manipulated by hand. These secondary instruments are often inserted into the patient's body through a separate port, and thus, while being used, are viewed from a different point of view in the visual image. Furthermore, the therapeutic instrument often blocks the practitioner's direct view of the ROI with the imaging tool, making highly accurate therapies quite difficult for the medical practitioner to achieve. Significant amounts of training and practice are required to overcome these difficulties, as well as the capability to work with a reduced sense of touch that is conveyed through the shaft of an instrument having friction and a non-intuitive pivot at the point of entry. Thus, to work effectively with current imaging and therapeutic technologies, the practitioner of MIMPs must be highly trained and skilled.

Clearly, there is a need for an imaging system that is small enough to be integrated with diagnostic and/or therapeutic functions to create an instrument that is sufficiently intuitive to use as to require little training or skill. Similarly, a small, integrated display system would greatly improve mobility for a head mounted display and enable very localized display of images. Ideally, an image acquisition or display system should integrate a light source, an actuation system, a position sensing system, light detectors, and a local control system, yet be smaller than currently available systems. Despite its small size, the integrated system should still be capable of providing a sufficient FOV, a good image size, and high resolution. The integrated system should also enable a practitioner to ensure that therapy can be administered to the ROI imaged within a patient's body. Currently, no integrated system is small enough to provide these capabilities and cannot be easily modified to provide such capabilities.

SUMMARY

This application specifically incorporates by reference the disclosures and drawings of each patent application and issued patent identified above as a related application.

In accord with the present invention, an apparatus is defined for providing image acquisition and/or image display in a limited ROI. The apparatus comprises a micro-electro-mechanical system (MEMS) that integrates needed components into a miniature device that can be produced with conventional micro-fabrication techniques. The apparatus preferably includes one or more integrated light sources such as one or more laser diodes for illuminating an ROI, displaying an image, providing a therapy, and/or performing another function. Alternatively, the light source can include a generation component and delivery component, whereby only the delivery component is integrated into the apparatus. The light source can further include a modulator or filter, or modulation and filtering can be performed on the input or output of the light source. Also included is a cantilever having a fixed end and a free end. The fixed end is attached to a substrate that supports many or all other components of the apparatus. Preferably, the free end of the cantilever is released from the substrate during fabrication of the cantilever such that the cantilever can move in two orthogonal directions. The cantilever also preferably comprises a light-transmissive material such as an epoxy resin that acts as a waveguide to direct light from the light source toward the ROI. In that case, the one or more light sources are optically coupled to the fixed end of the cantilever waveguide, and the free end of the cantilever waveguide is adapted to be positioned adjacent to the ROI. One or more scanning actuators are disposed adjacent to the cantilever and supported by the substrate. The scanning actuators cause the light from the free end of the cantilever to scan the ROI to illuminate the ROI for image acquisition or for image display. The light may pass through a lens attached to, or just beyond the fixed end of the cantilever. One or more position sensors also detect the position of the free end of the cantilever, providing feedback for control. When used for image acquisition, one or more light detectors receive light backscattered from the ROI, producing a signal corresponding to an intensity of the backscattered light. The signal can be used to produce an image of the ROI on a display. A control circuit is preferably coupled to the scanning actuators, the light sources, the position sensors, and the light detectors. The control circuit selectively energizes the one or more light sources to image the ROI, display an image in the ROI, and/or render another function to the ROI. Other functions can include diagnosing a condition, rendering therapy, sensing a condition, and monitoring a medical procedure—all in regard to the ROI. The control circuit can also provide long term control of scanning stability. The above components can be fabricated on multiple substrates, each substrate being best suited for a corresponding component. These subassemblies can then be bonded together or otherwise integrated to form the complete image acquisition and/or display device.

In an alternate embodiment of the present invention, light from the one or more light sources is directed along one or more stationary waveguides to illuminate the ROI. Backscattered light is then received at the free end of the cantilever, which may have a lens fabricated on the free end. The cantilever scans the backscattered light and directs the backscattered light to the fixed end where a light detector is optically coupled. Another embodiment does not require the cantilever to be a waveguide. Instead, a light source is located at the free end of the cantilever to directly scan into the ROI. Yet another embodiment uses a flexible fiber to receive backscattered light from the ROI and direct the light to a separate light detection component. It is also contemplated that a plurality of cantilever waveguides can be used in parallel to convey light to and from the ROI.

In another configuration, the free end of the cantilever waveguide is tapered to a substantially smaller cross-sectional size than the fixed end, producing a tapered end that emits light having a substantially smaller point spread function (PSF) than light that would be emitted from a non-tapered end. The tapered free end can also form a gradient index lens. Alternatively, a micro refractive lens can be provided at the free end of the cantilever. As another alternative, a diffractive lens can be micro-fabricated at the free end. In addition, or alternatively, a lens can be provided between the ROI and the light detectors and/or between a therapeutic light source and the ROI.

One form of the scanning actuator includes one or more electrostatic actuators that use electrostatic forces to preferably move the free end of the cantilever in substantially transverse directions. In another embodiment, the scanning actuator comprises one or more piezoelectric actuators that harness the piezoelectric effect to move the free end of the cantilever. Other actuation methods can be employed, although it is preferable to use actuation methods that can be integrated into the apparatus with conventional micro-fabrication techniques. In any case, the actuators can be used to drive the cantilever into resonance with one or more nodes. The free end can then scan the ROI in a raster, spiral, or other pattern. Alternatively, the actuators can be used to selectively drive the free end to precise positions.

Additionally, the position sensors can be used for feedback control of the free end of the cantilever. Similar to the scanning actuators, multiple embodiments of the position sensors can be implemented. The scanning actuators can be used in an alternating fashion to drive and detect the free end of the cantilever. Preferably, however, separate transducers are integrated into the waveguide or substrate to detect the position of the free end in orthogonal directions. The transducers can comprise piezoelectric detectors, capacitive sensors, piezoresistive sensors, or other micro-fabricated position sensors. Position of the free end can also be determined by detection of light lost or light scattered from the cantilever waveguide.

Another aspect of the invention comprises a method for enabling either far-field image acquisition or display of an image in a limited ROI. The method includes forming a cantilever on a substrate, and removing a portion of the substrate underlying the cantilever so that the cantilever can be deflected. The method also includes supporting the cantilever at a fixed end so that the fixed end remains fixed to the substrate, and a free end of the cantilever extends freely beyond where the portion of the substrate was removed from supporting the cantilever. This enables the free end to move relative to a target in the limited ROI. The cantilever is deflected so as to move the free end in a desired motion. The cantilever conveys light, so that if the cantilever is employed for acquiring the far-field image, the light is reflected from a target and conveyed from the free end toward the fixed end. Alternatively, if the cantilever is employed for displaying the image, the light is emitted toward the target from the free end. The method further includes detecting a position of the free end of the cantilever, and producing a signal indicative of the position for use in controlling the cantilever to move in the desired motion. Other aspects and details of the invention are described in further detail below.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein.

Figure 2A:
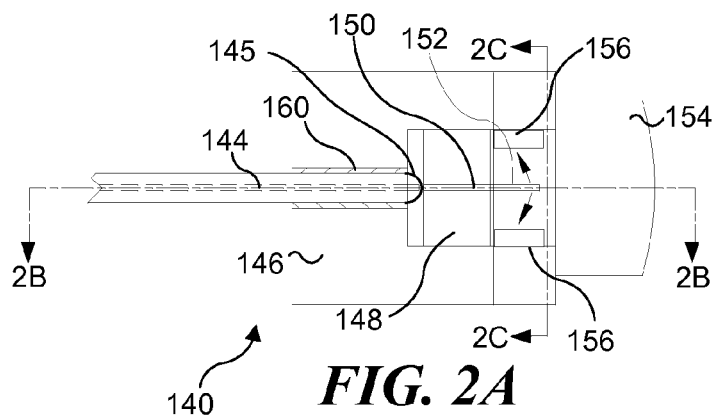
Figure 2B:
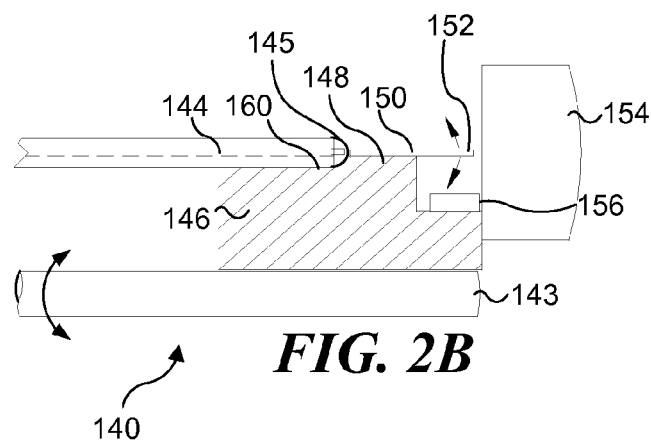
Figure 2C:
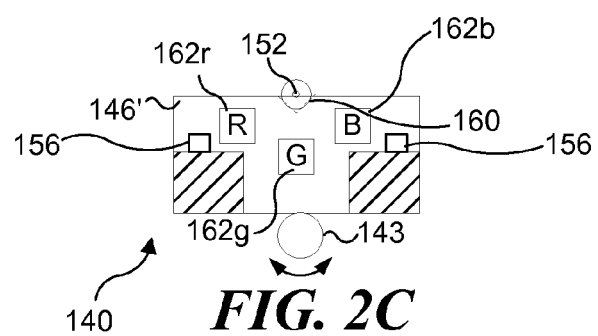
Figure 2D:
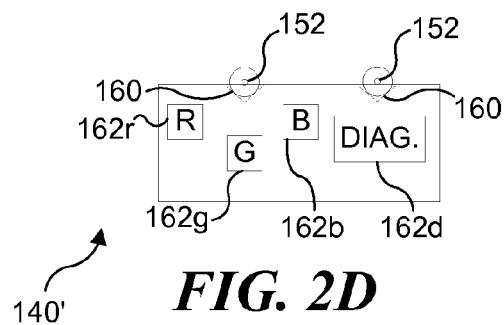
Figure 3:
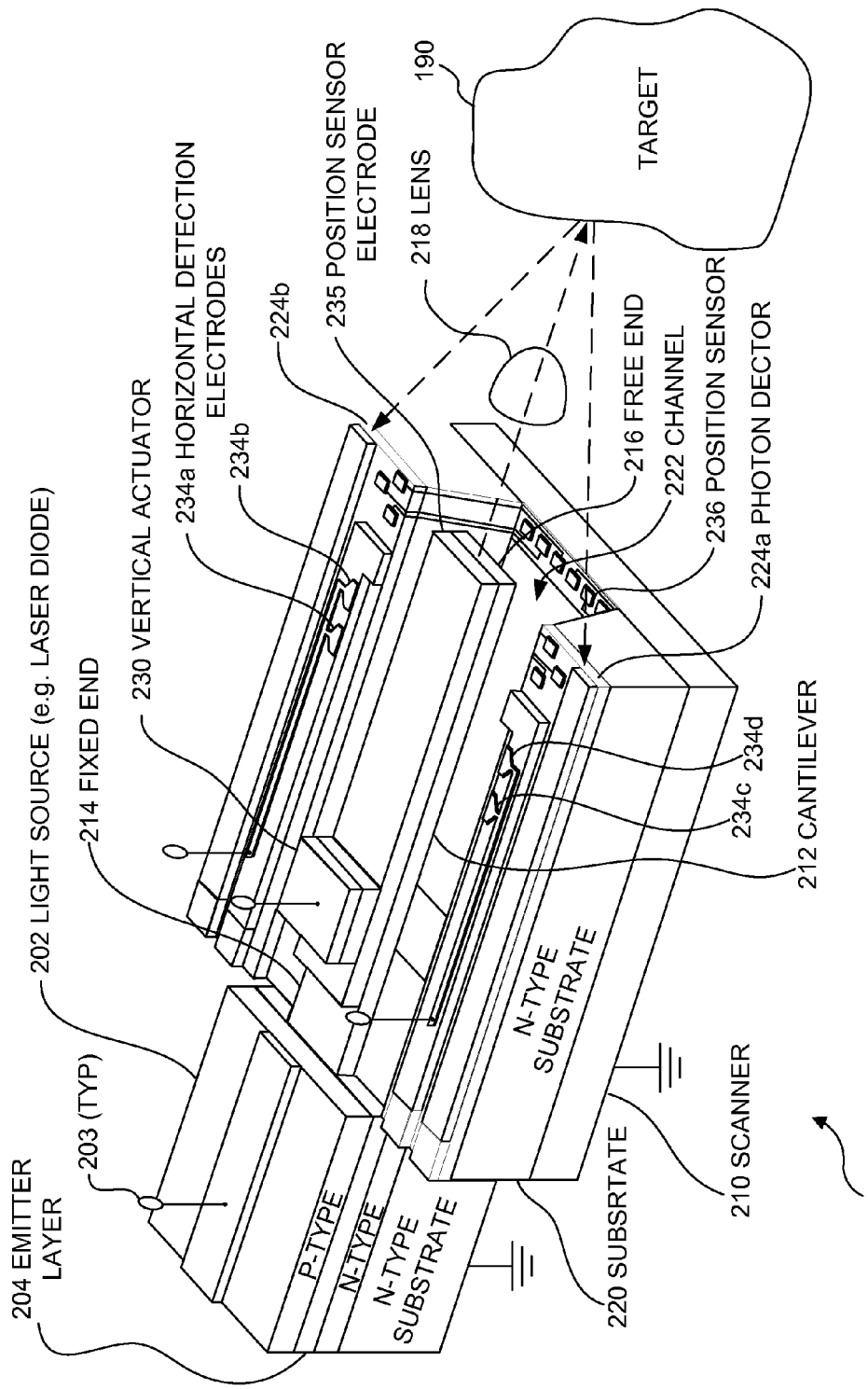
Figure 4:
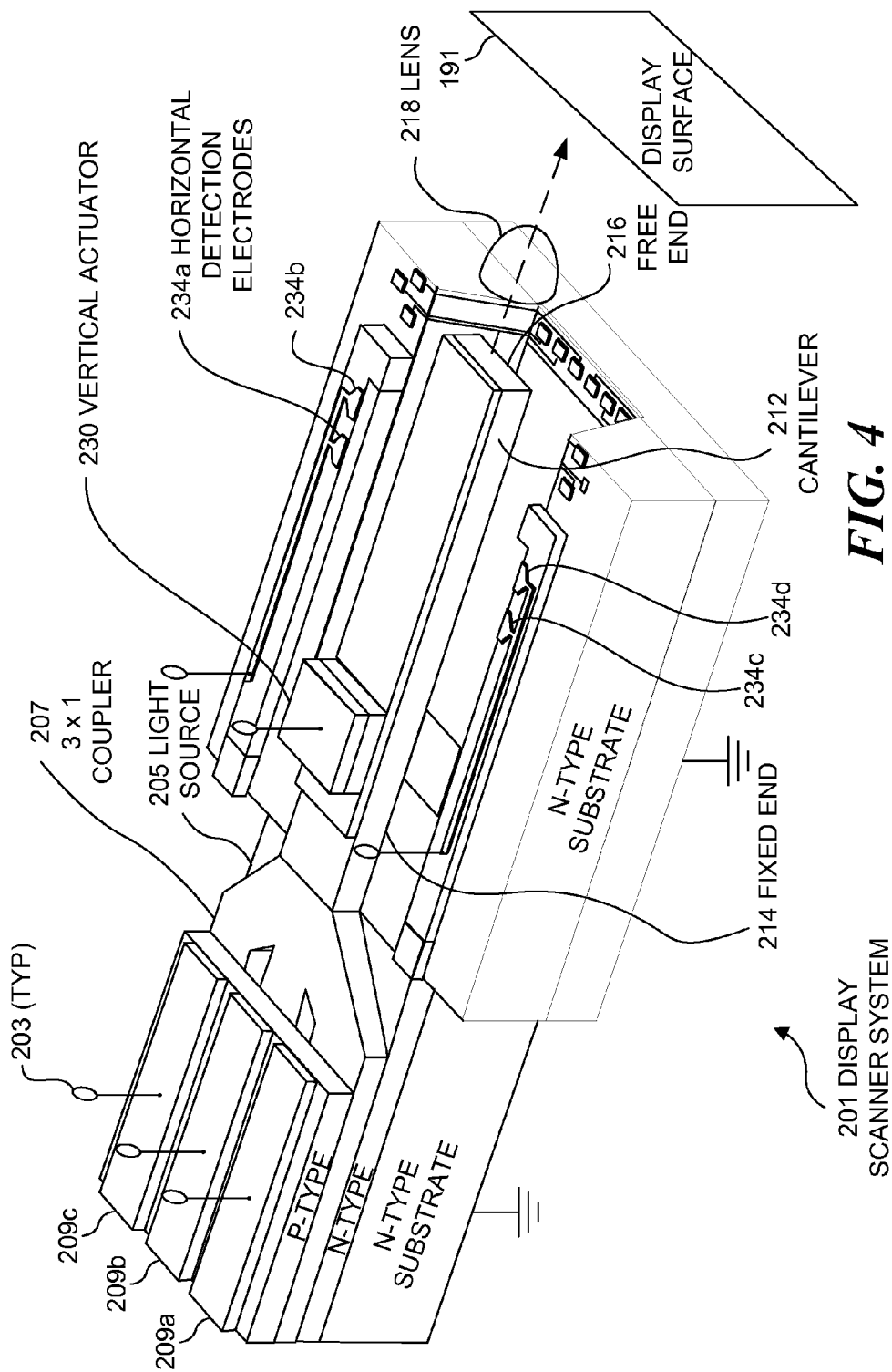
Figure 5:
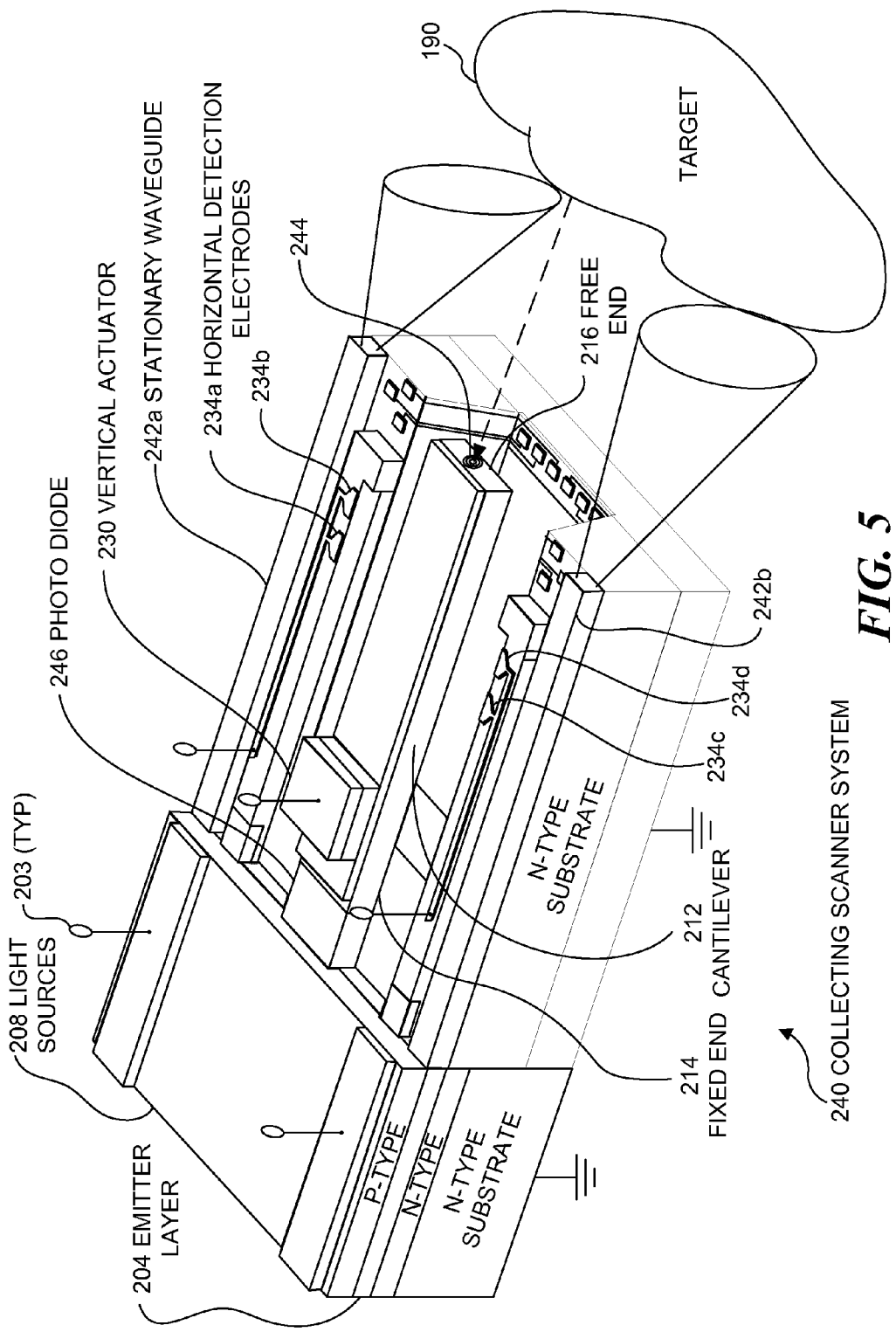
Figure 6A:
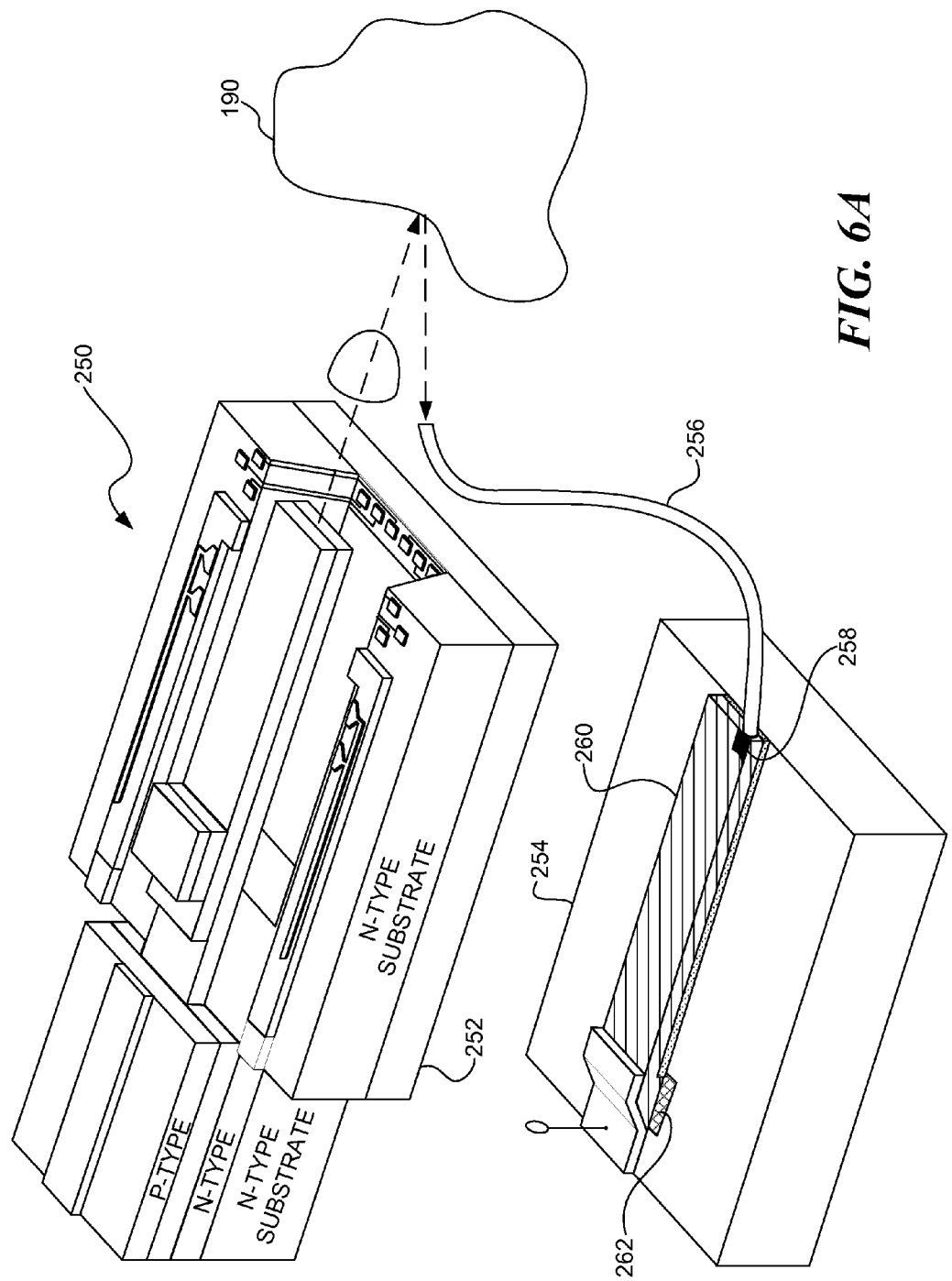
Figure 7A:
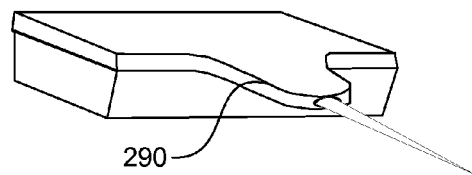
Figure 7B:
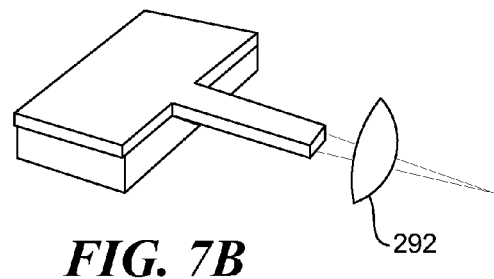
Figure 7C:
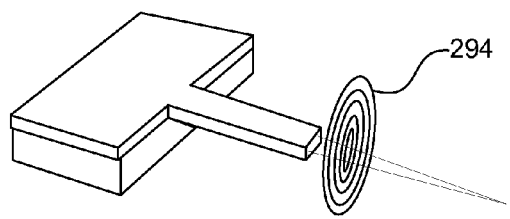
Figure 7D:
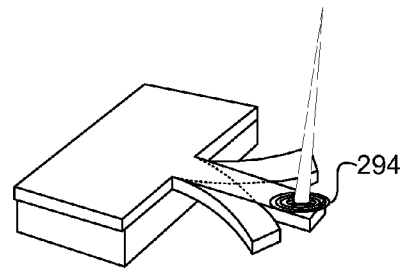
Figure 8A:
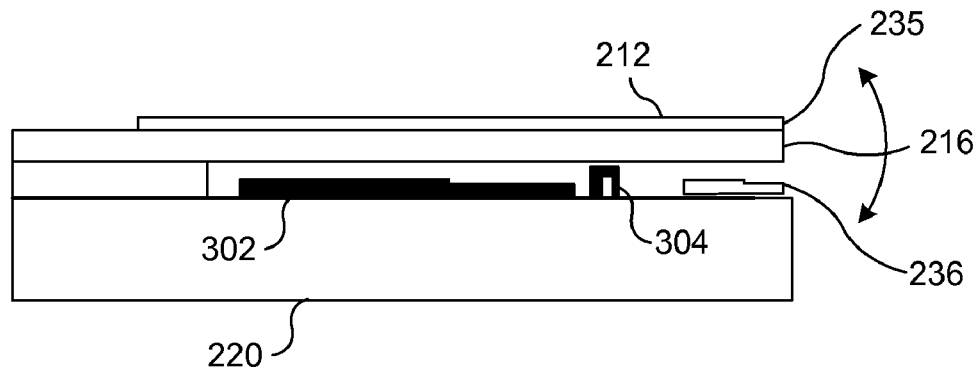
Figure 8B:
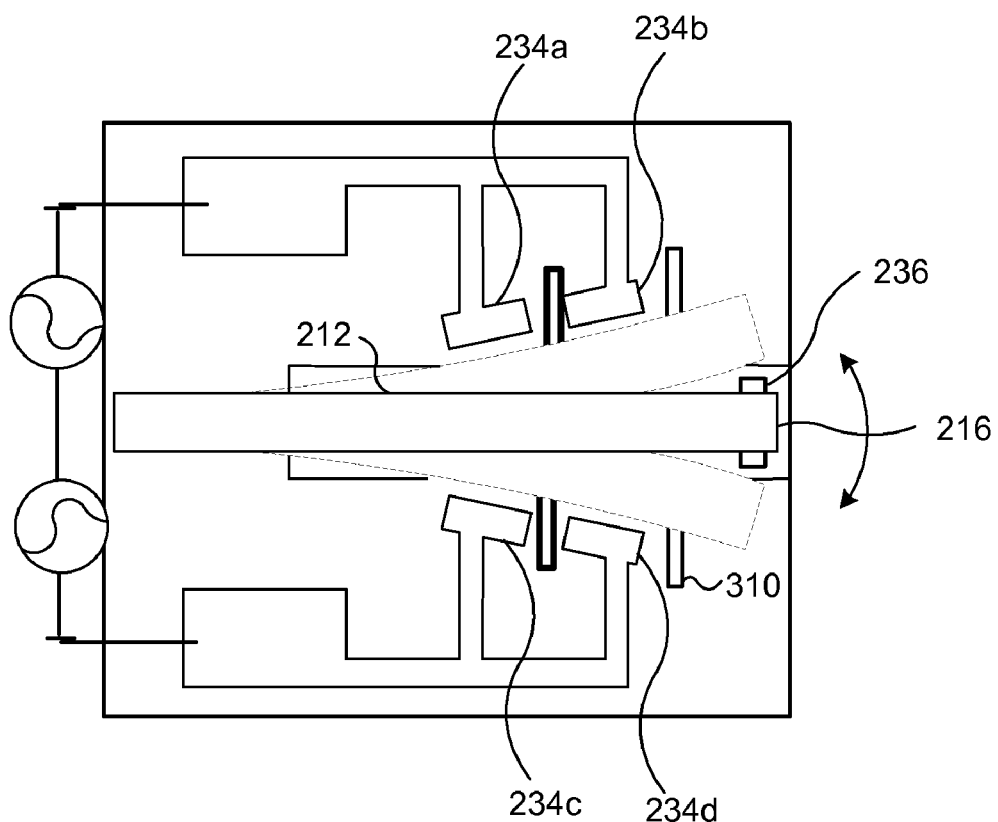
Figure 9A:
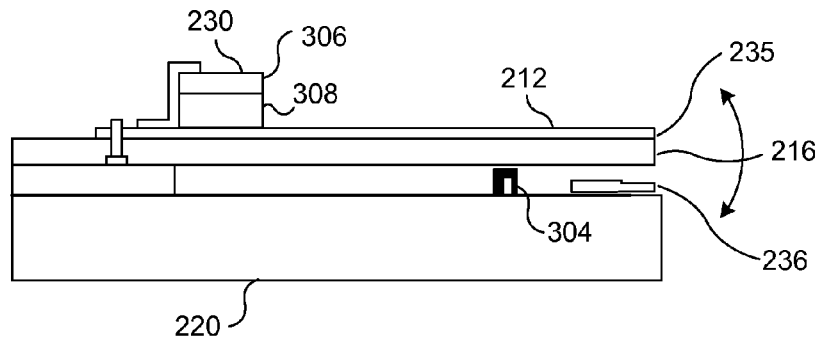
Figure 9B:
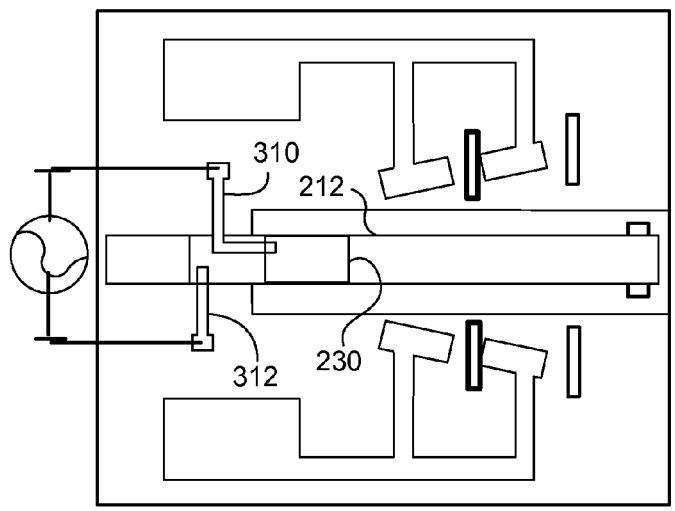
Figure 10A:
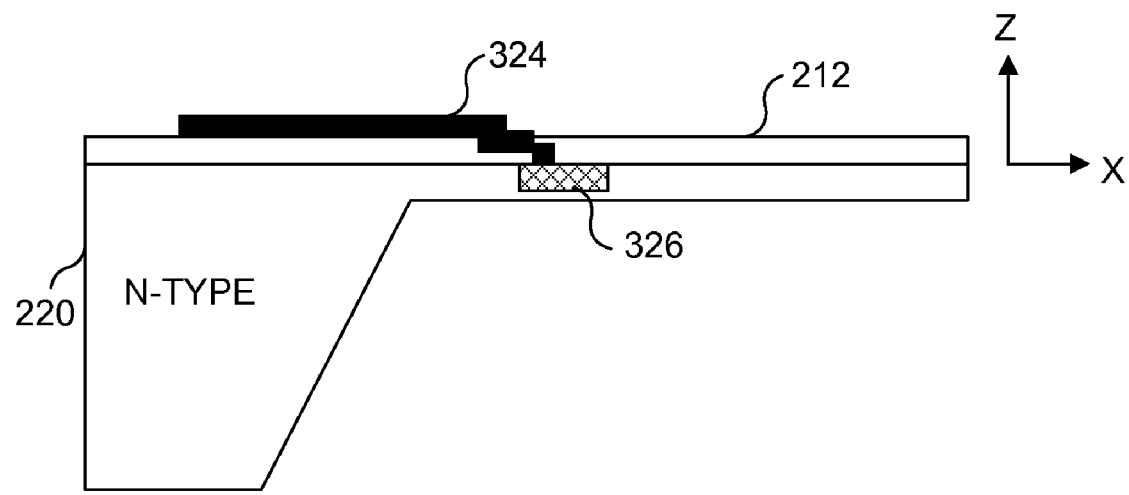
Figure 10B:
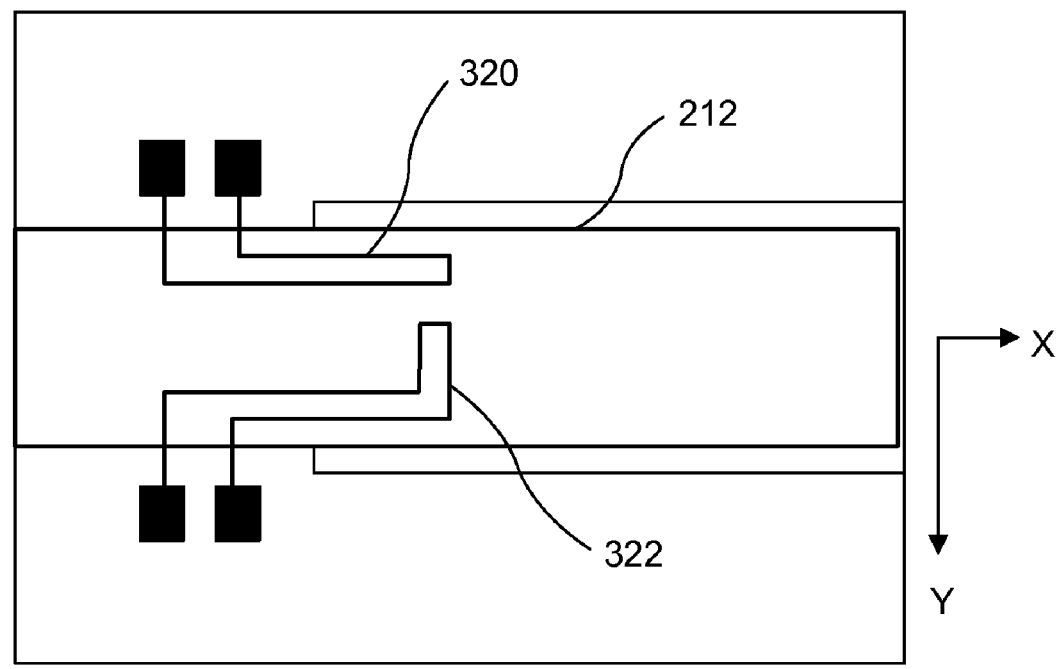

FIGS. 2A, 2B, and 2C respectively illustrate a top plan view, a side elevational cross-sectional view taken along section line 2B-2B in FIG. 2A, and an end view taken along section line 2C-2C in FIG. 2A, of a first prototype embodiment of a thin film, rectilinear illuminator;

FIG. 2D illustrates an end elevational view of a second prototype embodiment that includes a pair of thin film parallel cantilevers for illumination of an ROI;

FIG. 3 is an isometric view of an integrated image acquisition scanner system;

FIG. 4 is an isometric view of an integrated display scanner system;

FIG. 5 is an isometric view of an integrated collecting scanner system;

FIG. 6A is an isometric view of a hybrid emitting scanner system;

FIG. 6B is an isometric view of a cantilevered laser diode system;

FIG. 6C is an isometric view of a cantilevered fiber waveguide system;

FIG. 7A is an isometric view of the free end of the cantilever waveguide formed into a gradient index lens;

FIG. 7B is an isometric view of the cantilever waveguide with a micro refractive lens;

FIG. 7C is an isometric view of the cantilever waveguide with a Fresnel lens;

FIG. 7D is an isometric view of the cantilever waveguide with a Fresnel lens microfabricated on to an upper surface of the cantilever waveguide;

FIG. 8A is a side sectional view of a scanner showing a vertical actuator that utilizes electrostatic force;

FIG. 8B is a plan view of a scanner showing a horizontal actuator that utilizes electrostatic force;

FIG. 9A is a side sectional view of the scanner showing a layered configuration of a vertical actuator that utilizes the piezoelectric effect;

FIG. 9B is a plan view of the scanner illustrating a configuration of traces for energizing conductive layers for the vertical actuator that utilizes the piezoelectric effect;

FIG. 10A is a side sectional view of a scanner with a piezoresistive transducer integrated into the cantilever; and FIG. 10B is a plan view of the scanner with two piezoresistive transducers integrated into the cantilever for measuring vertical and horizontal motion of the cantilever.

DESCRIPTION

Figures and Disclosed Embodiments Are Not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

Example Applications of the Present Invention

As indicated above, the present application is a continuation of a copending patent application Ser. No. 10/655,482, filed on Sep. 4, 2003, which itself is a continuation-in-part of prior copending patent application Ser. No. 09/850,594, filed on May 7, 2001, and now issued as U.S. Pat. No. 6,975,898, which is based on prior copending provisional patent application Ser. No. 60/212,411, filed on Jun. 19, 2000, all of which are hereby explicitly incorporated by reference. These applications describe a medical imaging, diagnostic, and therapy device. However, the present invention may be used for acquiring an image, for displaying an image, or for otherwise detecting or delivering light. Nevertheless, for exemplary purposes, the present invention is primarily described with regard to a preferred embodied as a miniature medical device such as an endoscope. Those skilled in the art will recognize that the present invention can also be embodied in a non-medical image acquisition device, a wearable display, a biological, chemical or mechanical sensor, or any other miniature high resolution, far-field device. For example, the invention can be used to illuminate specific patterns for microlithography, micro-inspection, and micro-illumination. The invention can further be embodied in a bar code reader, a range finder, or a device for combining simultaneous sensing and delivery functions.

As an endoscope, the present invention can be used to integrate both imaging and non-imaging functionality, such as diagnosis, monitoring, and therapy of an internal ROI, instead of requiring separate instruments for imaging and for rendering therapy or other functions to a site. For example, an integrated endoscope can provide ultraviolet therapy and monitoring. Also, many optical diagnostic and therapeutic techniques rely on high quality illumination at elevated intensities, which is inherent in optical scanning and cannot be achieved with diffuse illumination. A scanned beam of intense optical energy is more effective at overcoming the signal-to-noise limitations of photon detectors used in conventional diagnostic imaging systems. When fluorescent dye molecules are used as tracers for specific cells or structures, the signal conversion rates from illumination to fluorescence are very low and often buried in noise. In many therapeutic applications, such as photodynamic therapy (PDT), the optical excitation of PDT labels on cancerous cells creates free radicals that kill nearby cells. Doses of intense optical illumination are applied to overcome the natural buffering mechanisms within the body, to attain effective concentrations of free radicals. Laser therapies that rely on optical heating, cutting, and cauterization of tissues require the highest optical intensities that can be delivered and cannot be used effectively with diffuse illumination. Directed, focused beams of light on tissue for precise exposure times are necessary for reducing surrounding tissue damage which is provided in a controlled optical scan system. Furthermore, high quality illumination can include a high degree of optical monochromaticity, coherence, polarization, high modulation frequency, high pulse repetition rates, and short pulse duration.

Image Acquisition System Processing Overview

Figure 1A:
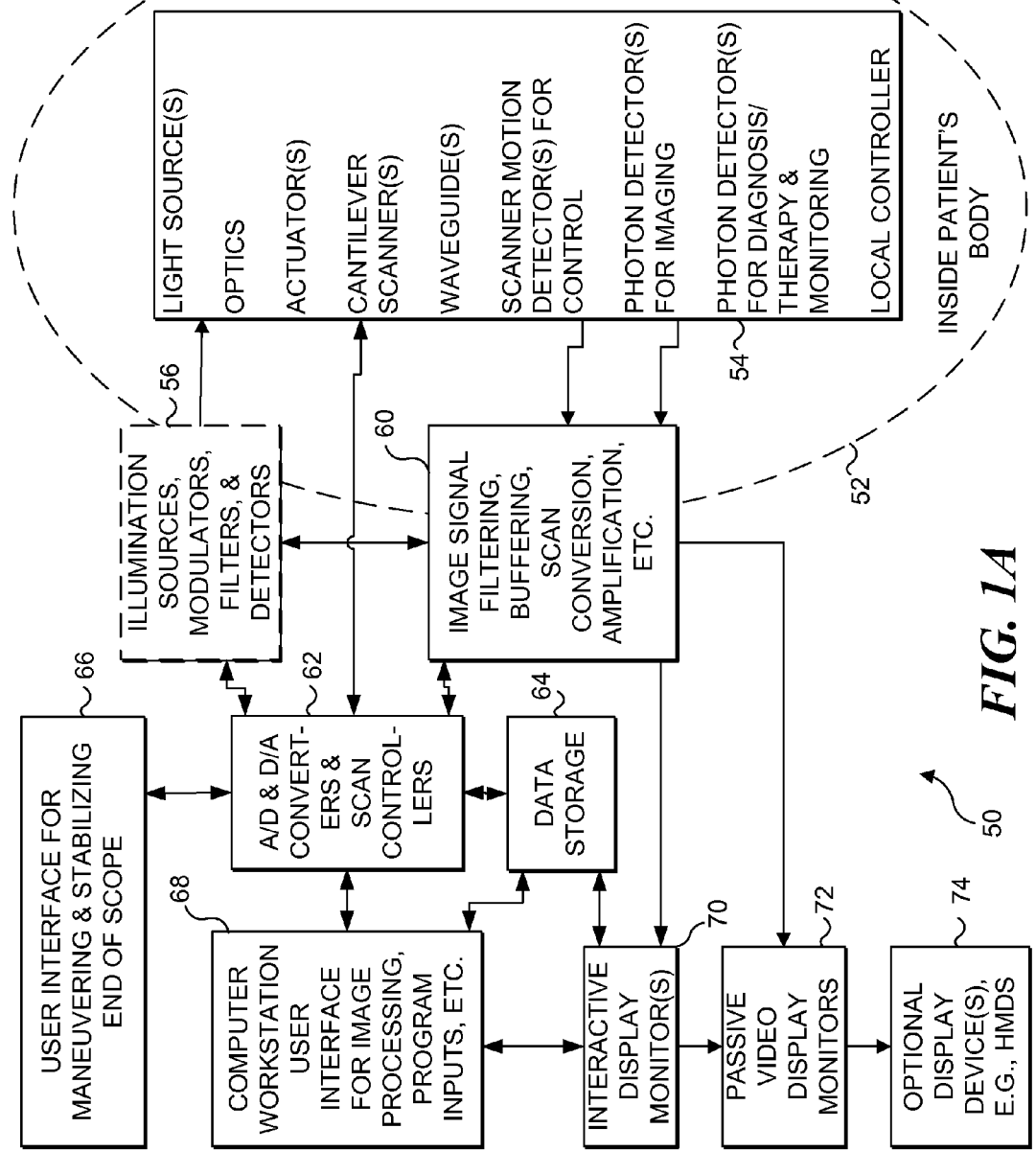
FIG. 1A is a functional block diagram illustrating an image acquisition system including supporting components for processing signals from, and controlling various components that are placed inside a patient's body.

An example system for providing imaging and non-imaging functionality through an endoscope is shown in FIG. 1A. More specifically, FIG. 1A illustrates a system 50 that shows how the signals produced by components of the integrated image acquisition device that is placed inside a patient's body are processed with external instrumentation and how signals used for controlling the system are input to the components that are inside the patient's body. In order to provide integrated imaging and other functionality, system 50 is thus divided into the components that remain external to the patient's body, and those which are used internally (i.e., the components within a dash line 52). A block 54 lists functional components of the integrated image acquisition device and/or other components disposed at the distal end of the endoscope. As indicated therein, these components preferably include one or more light sources, optical components, actuators, cantilever scanners, waveguides, lenses, photon detectors, motion detectors for motion control of the scanner(s) and/or control of the distal end of the endoscope, and/or photon detectors for imaging the ROI. Optionally, additional photon detectors may be included for diagnostic purposes and for therapy and monitoring purposes. Also optionally, one or more local controllers may be integrated for localized processing of control signals and detected signals. It should be noted that in regard to system 50, only the functional components actually required for a specific application may be included. Also, the additional functions besides imaging can include diagnosis, or therapy, or a combination of these functions.

Externally, additional or alternate illumination sources, modulators, filters, and detectors may be provided as shown in a block 56. For example, external light source systems for producing red, green, blue (RGB), ultraviolet (UV), Infrared (IR), and/or high intensity light may include a delivery component to convey light to the distal end of the endoscope. As illustrated, all or portions of the additional or alternate illumination sources may be partially, or completely inside the patient's body. For instance, additional light emitting diodes may be integrated with the components of block 54 at the distal end of the endoscope. For external illumination sources, modulators, filters, and detectors are also optionally coupled to the electromechanical scan actuator(s) inside the patient's body and to the scanner control actuators. Scanner motion detectors are used for controlling the scanning and produce a signal that may be fed back to the scanner actuators, illumination source, and modulators to implement scanning control.

In a block 60, image signal filtering, buffering, scan conversion, amplification, and other processing functions are implemented using the electronic signals produced by the imaging photon detectors and for the other photon detectors employed for diagnosis/therapy, and monitoring purposes. As illustrated, some or all of these functions may alternatively be implemented with integrated circuitry that is near the distal end of the endoscope inside the patient's body. Blocks 56 and 60 are interconnected bi-directionally to convey signals that facilitate the functions performed by each respective block. Similarly, each of these blocks is bi-directionally coupled in communication with a block 62 in which analog-to-digital (A/D) and digital-to-analog (D/A) converters are provided for processing signals that are supplied to a computer workstation user interface, shown in a block 68, employed for image acquisition, processing, for executing related programs, and for other functions. Control signals from the computer workstation are fed back to block 62 and converted into analog signals, where appropriate, for controlling or actuating each of the functions provided in blocks 56 and 60. The A/D converters and D/A converters within block 62 are also coupled bi-directionally to a block 64 in which data storage is provided, and to a block 66. Block 66 represents a user interface for maneuvering, positioning, and stabilizing the end of the scanning optical waveguide within a patient's body.

In block 64, the data storage is used for storing the image data produced by the detectors within a patient's body, and for storing other data related to the imaging and functions implemented by the scanning optical waveguide. Block 64 is also coupled bi-directionally to the computer workstation and to an interactive display monitor(s) in a block 70. Block 70 receives an input from block 60, enabling images of the ROI to be displayed interactively. In addition, one or more passive video display monitors may be included within the system, as indicated in a block 72. As indicated in a block 74, other types of display devices, for example, a head-mounted display (HMD) system, can also be provided, enabling medical personnel to view an ROI as a pseudo-stereo image. The HMD system can include a display embodiment of the invention to display the image acquired from within the patient's body. The display embodiment is effectively an inverse of the image acquisition system.

Display System Processing Overview

Figure 1B:
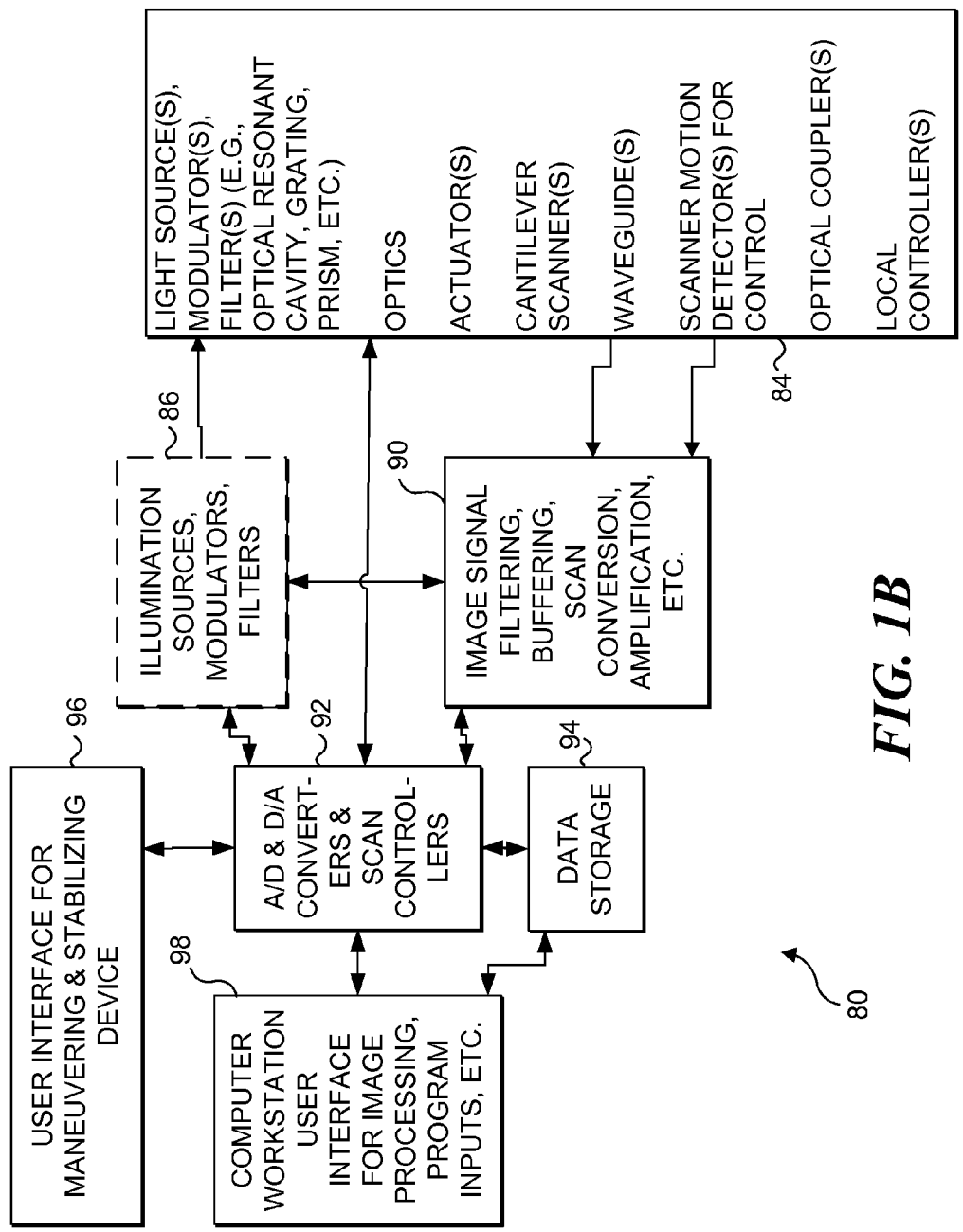
FIG. 1B is a functional block diagram illustrating a display system including supporting components.

An example system for providing display functionality is shown in FIG. 1B. System 80 shows how signals are processed by various components for display on a target surface in a ROI. A block 84 lists the functional components of an integrated display scanner. Similar to the image acquisition system discussed above, the components of the integrated display scanner preferably include one or more light sources, actuators, cantilever scanners, waveguides, lenses, local controllers, and tip displacement sensors. In addition, the integrated display scanner preferably further includes one or more light modulators and filters, although these components can be non-integrated, as shown in block 86. Photon detectors can be included for monitoring the displayed image and/or measuring motion of the cantilever scanner(s), but photon detectors are not required for a display device.

Other external or non-integrated components are similar to those used for the image acquisition system discussed above. For example, in a block 90, image signal filtering, buffering, scan conversion, amplification, and other processing functions are implemented. Blocks 86 and 90 are interconnected bi-directionally to convey signals that facilitate the functions performed by each respective block. Similarly, each of these blocks is bi-directionally coupled in communication with a block 92 in which analog-to-digital (A/D) and digital-to-analog (D/A) converters are provided for processing signals that are supplied to or by a computer workstation user interface, shown in a block 98, employed for image display, for processing, for executing related programs, and for other functions. Control signals from the computer workstation can be fed back to block 92 and converted into analog signals, where appropriate, for controlling or actuating each of the functions provided in blocks 86, 90 and 84. The A/D converters and D/A converters within block 92 are also coupled bi-directionally to a block 94 in which data storage is provided, and to a block 96. Block 96 represents a user interface for maneuvering, positioning, and stabilizing the end of the scanning optical waveguide for display. Block 94 is also coupled bi-directionally to the computer workstation, and the data storage is used for storing the image data, and for storing other data related to the display and functions implemented by the scanning optical waveguide. In addition, one or more passive video display monitors may be included within the system (not shown) for test purposes. Further detail is discussed below with regard to FIG. 4.

Prototype Fiberoptic-MEMS Hybrid Embodiment

As indicated above, it is desirable to produce a scanning device with a small cross-sectional area that can be produced at relatively low cost and high volume to make endoscopes and other imaging and display devices more economical and thereby facilitate their widespread use as disposable devices. Micro-electromechanical systems (MEMS) technology makes these goals achievable using an integrated thin film device. FIGS. 2A, 2B, and 2C illustrate an early prototype of a thin film optical system 140, in which this approach was shown to be effective. A further alternative 140' illustrated in FIG. 2D includes parallel cantilevered thin film optical waveguides for scanning and detectors.

In this embodiment, electrostatic actuators 156 act on a thin film optical waveguide 150 that is supported on a raised ledge 148. The thin film optical waveguide is only approximately 0.003 mm in diameter. A distal portion 152 of the thin film optical waveguide is caused to scan in the two orthogonal directions indicated by the curved arrows in FIGS. 2A and 2B. It should be noted that the scanning motion can be one-dimensional (i.e., along a single axis), or as shown, in two dimensions (e.g., along a raster pattern or a spiral pattern). Optionally, the thin film optical device can be mounted on a rod 143, which is then manually or mechanically rotated or vibrated to change the orientation or displace the single axis scan. Also provided is a lens 154 that is preferably mounted to a silicon substrate 146 (or other substrate material). As an alternative, external actuators (not shown) can be used instead of the electrostatic actuators, in which case, an optical fiber 144 and lens 154 would be supported by silicon substrate 146, which would be caused to vibrate by the external actuators, causing the cantilevered thin film optical waveguide to resonantly scan.

Optical fiber 144 is preferably affixed to silicon substrate 146 within a centering V notch 160 to ensure that it is aligned with thin film optical waveguide 150. Since the optical fiber is approximately 0.1 mm in diameter, care must be taken to provide accurate alignment between the ends of the optical fiber and the thin film optical waveguide. FIGS. 2A and 2B show the embodiment using butt-end coupling between optical fiber 144 and a thin film optical waveguide 150. To ensure appropriate alignment between the optical fiber and the thin film optical waveguide, V notch 160 precisely establishes a disposition of the optical fiber relative to the thin film optical waveguide. An index-matching gel 145 or fluid can be used to couple light from optical fiber 144 to thin film optical waveguide 150. To reduce the gap filled by index-matching gel 145, the tip of the optical fiber can be etched to form a taper. Further, the tip length and surface can be adjusted by $CO_2$ laser machining before affixation. Other embodiments described below further alleviate alignment problems.

In the view of the embodiments shown in FIGS. 2A, 2B and 2C, light reflected back from a target in the ROI passes through lens 154 and is received by RGB detectors 162*r*, 162*g*, and 162*b*, respectively. These detectors respond to the light of the corresponding color, producing a signal that is conveyed proximally to the external components, as discussed above. In FIG. 2D, separate image and diagnostic/therapeutic thin film optical waveguides are spaced apart and scanned in parallel; this embodiment uses a diagnostic "DIAG" detector 162*d*.

Integrated Image Acquisition Emitting Scanner Embodiment

Further detail is now provided regarding preferred embodiments. FIG. 3 is an isometric view of an integrated emitting scanner system 200. Emitting scanner system 200 can perform image acquisition and/or display by directing emitted light with a flexible cantilever. However, for discussion purposes, emitting scanner system 200 will be described primarily with regard to image acquisition. In general, an image is acquired by scanning a waveguide and capturing the image with one or more stationary light detectors. Preferably, the waveguide will be driven to resonance, but motion is not restricted to operating at resonance. In any case, rather than generating and sampling an image plane as is done using conventional micro-image acquisition devices, which typically use either a bundle of optical fibers or a camera with an array of detectors, an image plane is generated by scanning light from the single resonant waveguide. For some applications this approach is beneficial, since it is capable of providing a wide optical field of view (FOV) in a relatively small movement volume. This approach also provides high image resolution, because an illuminated spot size determines pixel resolution rather than a sample area size. Thus, the detector size and number do not affect the image resolution. Image resolution can also be altered to create a zoom mode by changing scanning amplitudes and/or the sampling rate of the light detector.

Emitting scanner system 200 creates an illuminated spot on a target 190 by scanning light from a light source 202. Light source 202 preferably comprises a semiconductor device such as a light-emitting diode (LED) or a laser diode, so that the light source can be fabricated along with a scanner 210 using conventional micro-fabrication techniques. However, as suggested above, an external light source can alternatively be coupled to scanner 210 with an optical fiber or other waveguide. Preferably, when voltage is applied to light source 202 from a power lead 203, an emitter 204 generates light. Light source 202 is preferably end-butted to cantilever 212, which acts as a waveguide to direct emitted light from a fixed end 214 to a free end 216.

Fixed end 214 is attached to a substrate 220 such as n-type silicon. During fabrication of emitting scanner system 200, substrate 220 is etched to create a channel 222 into which free end 216 can deflect. Free end 216 may include a lens 218 to collimate or focus the light onto target 190. Free end 216 is preferably driven into resonance in one or more orthogonal directions to create an illuminated spot on target 190. For example, a vertical actuator 230 can deflect cantilever 212 in a vertical direction relative to a primary plane of substrate 220. Similarly, a horizontal actuator can be implemented with deflection electrodes 234*a*-234*d* to deflect cantilever 212 in a horizontal direction relative to the primary plane of substrate 220. By controlling the vertical and horizontal deflections, free end 216 can illuminate target 190 in a raster scan pattern, a spiral pattern, or other pattern. Alternatively, those skilled in the art will recognize that the free end can be deflected into a two-dimensional circular motion or into a two-dimensional rocking motion using a single actuator. The illumination can be used for acquiring an image, displaying an image, performing a therapy, or performing another function. For image acquisition, the image created from the backscattered light is captured by hybrid photon detectors 224*a* and 224*b* that are integrated onto substrate 220. Position sensor array 236 detects the vertical and horizontal position of free end 216 as a function of a conductive layer 235 that is integrated onto cantilever 212. This or other position sensor implementations enable long term control of scanning stability.

Integrated Display Scanner Embodiment

FIG. 4 is an isometric view of an integrated display scanner system 201 for generating an image on a display surface 191. An RGB light source 205 is preferably used to generate the display light. However, a light delivery component of an external light source can be used. RGB light source 205 is preferably implemented with different colored LEDs 209*a*-209*c*, which preferably include different concentrations of dopant to create different wavelengths of light. The RGB lights are coupled via a 3×1 coupler 207 to fixed end 214 of cantilever 212, which acts as a waveguide to scan the light for display. Alternatively, a white light source with a built-in tunable color filter can be used. The built-in tunable color filter can be in an interferometer, grating, or prism configuration to provide the preferred color light to the scanner. The tunable filter is controlled by a light modulating circuit (not shown) based on the information provided from image processing software. Thus, a more definite color light is possible. Using a tunable filter also eliminates the need for three color input. The light can alternatively be delivered via a fiber that is coupled to the scanning cantilever waveguide. The image to be displayed is converted to binary code using image processing software. Output codes are then downloaded to a microprocessor (not shown) coupled to the light modulating circuit (not shown). The lights are strobed at a frequency based on the information provided by the microprocessor. An integrated lens or an external lens 218 is placed near the tip to provide the magnification needed for the image display.

As with the image acquisition system, mechanical scanning is provided by vertical actuator 230 and horizontal actuators 234*a*-234*d*. The position of free end 216 is monitored by the same type of position sensors as used for the image acquisition system. The information provided by the position sensors is used by an actuator control circuit to maneuver, position and/or stabilize free end 216 for creating the displayed image.

Integrated Image Acquisition Collecting Scanner Embodiment

An alternative preferred embodiment is provided for image acquisition. FIG. 5 is an isometric view of an integrated collecting scanner system 240. In this embodiment, cantilever 212 is used for image capture. This approach is less efficient than the emitting scanner system described above, because the resolution is limited by the numerical aperture of the image detection system used (e.g., the lens, waveguide, and detector). However, this approach is useful for specialized imaging and optical sensing where full illumination of the target and the image detector is required. In this embodiment, light is generated by one or more laser diodes 208 with emitter layer 204 butt-end coupled to, and aligned with one or more stationary semiconductor waveguides such as stationary waveguides 242*a* and 242*b*. The light is directed along the stationary waveguides and onto target 190. The back scattered light is received with cantilever 212, which is preferably driven in a rectilinear scanning motion by vertical actuator 230 and the horizontal actuator implemented with deflection electrodes 234*a*-234*d*. The back scattered light may pass through a lens 244 such as a diffractive lens. When received by cantilever 212, the light is directed back to a photodiode 246. Alternatively, the photodiode can be integrated into the free end 216 of the cantilever.

Integrated Hybrid Embodiments

As an alternative to collecting scanner system 240 and emitting scanner system 200 described above, a number of hybrids of the two systems can be implemented. For example, FIG. 6A is an isometric view of a hybrid emitting scanner system 250 that includes a simplified emitting scanner 252 for scanning light onto the target, and a separate simplified collecting system 254 to receive and detect the backscattered light. Simplified emitting scanner 252 does not need the integrated photon detectors. Instead, a flexible optical fiber 256 can be positioned near the illuminated area of target 190 to receive the backscattered light. Flexible optical fiber 256 directs the received light through a coupler 258 to an optional semiconductor waveguide 260, which directs the light to one or more photon detectors 262. The primary advantage of a hybrid approach is that various substrate materials can by selected to optimize the performance of each component.

Another hybrid embodiment uses the cantilever to support and move the light source directly. For instance, FIG. 6B is an isometric view of a cantilevered laser diode system 270. Instead of using the cantilever as a waveguide, a laser diode 272 is attached to free end 216 of cantilever 212. In this case, cantilever 212 provides electrical connections to laser diode 272, rather than transmitting light from a laser diode optically coupled to cantilever 212. As a further alternative, all of cantilever 212 can be fabricated as a laser diode. Still further, FIG. 6C is an isometric view of a cantilevered fiber waveguide system 280. An optical fiber 282, that can be etched to reduce mass, is coupled to cantilever 212 so that light is emitted from free end 216.

Other hybrid approaches can be used that maintain an integrated system. For example, a parallel array of cantilevers could be fabricated adjacent to each other and actuated in one dimension, thus creating a light scan over an area. This device would not require the relatively fast scan rates and large amplitudes of a single scanning waveguide. As a further example, the functional components, such as the laser diode light source, the waveguide, the photodiodes, the coupler, the position sensors and actuators can be integrated on separate substrates, each consisting of stacked functional modules. The light source might use a different substrate from that supporting the cantilever. For instance, GaAs can be used for the laser diode substrate for its ideal optical emission spectrum and output power efficiency. Further details regarding embodiments of the components comprising collecting scanner systems and emitting scanner systems are described below.

Cantilever

To balance the need for the cantilever to transmit light and mechanically resonate, a number of alternative materials or material combinations are possible. In one embodiment, the cantilever comprises a two-layer composite of silicon dioxide ($SiO_2$) and silicon. The $SiO_2$ is used as an optical core through which the light travels. However, as a thermal oxide, $SiO_2$ has less-than-desirable mechanical properties. Thus, a thin $SiO_2$ layer of approximately 2.2 micrometers ($\mu m$) is thermally grown on a layer of single crystal silicon that is approximately 30 $\mu m$ thick. The silicon layer gives the composite cantilever increased mechanical stiffness and durability. It is also preferable to include a low index buffer layer to optically isolate the silicon layer from the $SiO_2$ layer, because silicon has a high index of refraction and is absorbing in the visible band. However, for a short length cantilever such as less than 2 mm, the buffer layer can be omitted without excessive optical power loss.

Alternatively, a film of silicon nitride ($Si_xN_y$), or other compound can be used as the waveguide. However, a thick ($Si_xN_y$) film (e.g., >1 $\mu m$) cantilever waveguide can be difficult to fabricate. It is also difficult to align the thin optically transmissive layer with the emitter of an integrated light source, and even more difficult to align the thin optically transmissive layer with a fiber from an external light source. Thus, a preferred cantilever embodiment includes a thicker cantilever waveguide comprised of a mechanically durable material that still provides good optical transmission. One such material, which is also well suited to micro-fabrication, is SU-8 photoresist, originally developed by IBM™ (see U.S. Pat. No. 4,882,245). SU-8 offers beneficial imaging capabilities such as vertical sidewall profiles and dimensional control over an entire structure height. In addition, high functionality results in minimal swelling. Processing advantages include a highly cross-linked structure, which results in chemical resistance and high thermal characteristics and processing to greater than 200° C. As an epoxy based resin, SU-8 offers good adhesion to most surfaces as well as improved wetting on silicon glass, metals, and other low surface energy substrates. With its exposure near ultraviolet (UV) wavelengths (350-400 nm), SU-8 is a cost effective alternative to expensive X-ray processing.

Thus, cantilever 212 preferably comprises an SU-8 cantilever waveguide that is approximately 85 $\mu m$ thick at the fixed end and tapered to fit within a smaller diameter toward the free end. Cantilever 212 is also approximately 125 $\mu m$ wide, and approximately 0.5 mm to 1.0 mm long from fixed end 214 to free end 216. An overall larger coupling area at the fixed end makes it much easier to couple a light source to the cantilever waveguide, and increases the amount of light coupled into the cantilever waveguide. To further assist optical coupling, a tapered waveguide coupler (not shown) can be fabricated between the light source and the cantilever waveguide (or stationary waveguides). The SU-8 epoxy resin also makes the cantilever waveguide more durable. Although the modulus of elasticity of SU-8 (4.02 GPa) is less than the $SiO_2$/Si composite beam (silicon 125 GPa and silicon oxide 57 GPa), the increased thickness of the SU-8 cantilever waveguide results in resonant frequencies of approximately 20 kHz, which is typical of sVGA video rates.

Cantilever 212 is preferably formed by first spin coating the SU-8 photoresist onto the silicon substrate. The SU-8 is exposed with a mask to define the shape of the cantilever. The unexposed SU-8 is removed with a developing solution. A deep reactive ion etching (REI) process then etches the silicon substrate down to near the fixed end to release the SU-8 cantilever. A detailed description of the fabrication steps and REI process are provided in "Development of a Microfabricated Scanning Endoscope Using SU-8 Based Optical Waveguide" (Wei-Chih Wang, Reynolds Panergo, and Per Reinhall, Proceedings of Society of Photo-Optical Instrumentation Engineers, September 2003) and "Deep Reactive Ion Etching of Silicon Using an Aluminum Etching Mask" (Wei-Chih Wang, Joe Nhut Ho, and Per Reinhall, Proceedings of Society of Photo-Optical Instrumentation Engineers, Vol. 4876, 2003), both of which are hereby explicitly incorporated by reference. Other layers of material and micro-fabrication steps can be used to create the other integrated components along with one or more cantilevers.

Cantilever 212 can also be tapered with fixed end 214 being wider than free end 216. Tapering increases angular tip deflection, which provides a larger FOV. However, increased tip deflection may have to be balanced against the overall device size that is desired for a given application. Tapering can also be used to reduce the effective point source size of light emitted from the cantilever.

Lens

A variety of lenses can be implemented at the free end of the cantilever waveguide or stationary waveguides. FIGS. 7A-7D illustrate some of the possible lens implementations. FIG. 7A is an isometric view of the free end of the cantilever waveguide formed into a gradient index lens 290. FIG. 7B is an isometric view of the cantilever waveguide with a micro refractive lens 292 placed near the free end to focus the light onto the target. Micro refractive lens 292 can be fabricated from fused silica or $SiO_2$ or any other waveguide material using standard solid-state process. Micromolding techniques using silicone rubber and positive photoresist can also be employed. FIG. 7C is an isometric view of the cantilever waveguide with a Fresnel lens 294 placed at the free end. The number of bands and the separation between each band can be adjusted piezoelectrically to control the central maximum of the light beam and its focal length. FIG. 7D is an isometric view of the cantilever waveguide with Fresnel lens 294 microfabricated on to an upper surface of the cantilever waveguide.

Actuators

A variety of actuators can be implemented to drive the cantilever. One embodiment utilizes electrostatic force. An electrostatic actuator is advantageous for a number of reasons, including:

- it involves a very simple mechanism comprising a condenser of two conducting surfaces;
- it can be used as a driver as well as a position sensor for the cantilever; and
- the fabrication techniques used in device manufacture are compatible with mass production using the existing micro-fabrication technology, providing low device costs and high production yields.

FIG. 8A is a sectional view of a scanner showing a vertical actuator that utilizes electrostatic force. Unlike vertical actuator 230 shown in FIGS. 3-6C, in an electrostatic configuration, an electrode pad 302 is deposited onto substrate 220 under cantilever 212. Electrode pad 302 is preferably fabricated from an electrically conductive thin film such as Al, Ag, Au, Pt or Cu. When a voltage is applied between electrode pad 302 and substrate 220, an electrostatic force is generated between cantilever 212 and substrate 220. In practice, the electrode gap distance is limited to a few hundred microns. To induce a continuous motion on the cantilever, a sinusoidal voltage is applied to electrode pad 302. A bumper 304 can be fabricated under the cantilever to prevent the displaced cantilever from touching position sensor 236. The cantilever also acts as an isolator between electrode pad 302 and conductive layer 235. This prevents conductive layer 235 from sticking to substrate 220.

For two dimensional rectilinear raster scanning, the cantilever is scanned in two orthogonal axes simultaneously. To produce such a scan, a second set of independent and orthogonally oriented deflection electrodes are used to control the horizontal motion of the cantilever. FIG. 8B is a plan view of a scanner showing a horizontal actuator that utilizes electrostatic force. Horizontal deflection electrodes 234a-234d comprise the horizontal actuator. Voltage is selectively applied to a pair of electrodes on one side of cantilever 212 (e.g., horizontal deflection electrodes 234a and 234b). The voltage creates an electrostatic force that draws cantilever 212 toward the energized pair of electrodes. To induce resonance, a sinusoidal voltage is applied to one pair of horizontal deflection electrodes, while phase shifted sinusoidal voltage is applied to the opposite pair of horizontal deflection electrodes. The two sinusoids are 180 degrees out of phase with each other. One or more bumpers 310 can be used to limit the motion of free end 216. Also, as discussed above, an array of position sensors 236 can be used to detect the position of free end 216 to maintain control of cantilever 212.

Since the electrostatic actuator is not bandwidth limited by the scanning frequency, this technique can provide a higher scan rate than required by most standard video displays such as 31.5 kHz for VGA and 37.5-40 kHz for SVGA. Note, however, that for bidirectional scanning, the frequency of the cantilever need only be half of these stated values. Alternatively, a macro scale raster scanning device can be used as an identification (ID) scanner or a bar code scanner. For two dimensional nonrectilinear scans using single or dual actuators, the waveguide must be driven with a large base excitation to attain a large FOV. By controlling the excitation frequency, phase and amplitude, a steady in-and-out swirling scanning pattern can be achieved from free end 216. A circular scan pattern can be excited by applying excitation in horizontal and vertical directions ninety degrees out of phase. The circular pattern with varying radii can be controlled by the amplitude of the excitation. A rotating rectilinear scan pattern can be excited by applying electric potentials to two electrodes placed slightly at an angle to each other rather than orthogonal to each other. To generate the rotation on the rectilinear motion, a larger voltage must be applied to the electrodes for one direction (e.g., angled electrodes) than the voltage applied to the electrodes for the other direction (e.g., vertical electrodes). The result is a line sweep rocking back and forth between 0 and 180 degrees.

The relationship between deflection of free end 216 and the applied voltage can be nonlinear. To improve its linearity, an electrostatic comb drive can be used as the actuator such as that described by W. C. Tang et al. (*IEEE Sensors and Actuator Workshop. A*21, 23 (1990)). In a comb drive, the capacitance is varied through changing area, not the gap. Since capacitance is linearly related to area, the displacement will vary as the square of the applied voltage. In addition, harnessing the nonlinearity of cantilever deflection would be advantageous in that it would then be possible for a single actuator to generate two-dimensional (2D) motion of free end 216.

For vertical actuator 230 shown in FIGS. 3-6C, a piezoelectric effect is used. The advantages of using a piezoelectric driver include:

- the cantilever does not stick to the electrodes when it is driving too close to the substrate;
- the actuation mechanism would be highly resistive to environmental effect (e.g. humidity, temperature); and
- thin film deposition is compatible with VLSI processes (e.g. deposition methods and etching).

The disadvantage of using piezoelectric thin film for an actuator is that the actuator requires a high voltage for displacement in the micron regime. However, the problem can be partially alleviated by implementing a bimorph configuration. When mechanical pressure is applied to one of these materials, the crystalline structure produces a voltage proportional to the pressure. Conversely, when an electric field is applied, the structure changes shape producing dimensional changes in the material. Within certain range of electric and thermal stress, the voltage change ΔV gives rise to a corresponding force change ΔF based on $$\Delta V = d_{ij} x \Delta F / \epsilon_o \epsilon_r A$$

where dij is a charge sensitivity coefficient, x is the spacing between the two conducting plates of area A, and ∈o and ∈r are air and material dielectric constants, respectively. (For further detail, see G. S. Kino, *Acoustic Wave Device, Imaging & Analog Signal Processing* (1987)). The electromechanical materials preferably used for a microactuator are ZnO, lead zirconate titanate (PZT) and polyvinylidene fluoride (PVDF). A preferred way of depositing a ZnO thin film is to use a sputtering method. (For further detail, see S. B. Krupanidhi et al., *J. Appl. Phys.*, 56, 3308 (1984); B. T. Khuri-Yakub et al., *J. Appl. Phys.* 52, 4772 (1981)). Depositing PZT usually involves either sputtering or a sol-gel method, which is a method based on spin application of a chemical solution. (For further detail, see A. Okada, *J. Appl. Phys.*, 48, 2905 (1977); T. Tunkasiri et al., *J. Mat. Sci. Lett.*, 19, 1913 (2000); G. Yi et al., *J. App. Phys.*, 64, (1989); M. L. Wen et al., *Proceedings-of-the-SPIE*, 3892, (1999)). PVDF is preferably deposited as spin cast film from dilute solution in which PVDF powder has been dissolved.

FIGS. 9A and 9B show an example of a piezoelectric thin film actuator for the scanning system. Specifically, FIG. 9A is a side sectional view of the scanner showing a layered configuration of a vertical actuator that utilizes the piezoelectric effect. Vertical actuator 230 includes a conductive layer 306 comprising Cr/Au, Al, or other suitable conductive material. The same material is preferably used for cantilever conductive layer 235 that is deposited on the surface of cantilever 212. Between these conductive layers is an insulating layer 308 comprising a piezoelectric film such as ZnO, PZT, PVDF, or other suitable material. FIG. 9B is a plan view of the scanner illustrating a configuration of traces for energizing the conductive layers. A trace 310 is used to provide sinusoidal voltage to conductive layer 306. Another trace 312 is used to connect conductive layer 235 as a return reference.

As indicated by functional blocks 54 and 84 of FIGS. 1A and 1B, respectively, other techniques can be used to provide an actuator that can be integrated into a small area such as less than 3 mm. For example, optothermal excitation or thermal excitation can be used. For further detail, see R. J. Pitcher et al., Sensors and Actuators. A21, 387 (1990) and L. M. Zhang et al., *Sensors and Actuators. A* 21, 391 (1990). Another actuation method that uses a thermal effect is a shape memory alloy transducer. For further detail, see M. J. Zdeblick, *Design News*. (1993) and C. A. Ray et al., *San Francisco MRS Conf.*, (1992). Yet another method of actuation includes a magnetic actuator that passes current through coil loops to create a magnetic field that actuates the cantilever.

Position Sensors

A variety of position sensors can also be implemented to detect the position or other motion characteristic of the cantilever. The position sensor embodiment shown in FIGS. 3 through 6C uses a capacitive effect. The capacitive effect is one of the simplest precision sensing mechanisms for measuring displacement. A capacitive sensor detects changes in capacitance when the distance between two charged plates increases or decreases. Thus, capacitive sensor structures are relatively simple to fabricate. In general, a capacitive displacement sensor includes one moving plate and one fixed plate. As shown in FIG. 3, the moving plate corresponds to conductive layer 235 on top of cantilever 212. The fixed plate corresponds to position sensor array 236, which is located on substrate 220 in channel 222 under free end 216 of cantilever 212. An array of electrodes is used to enable position detection in both vertical and horizontal directions relative to a primary plane of substrate 220. Displacement in the horizontal direction is detected based on the area of each position sensor electrode that is covered by conductive layer 235 while cantilever 212 moves horizontally. Vertical displacement is detected based on the vertical distance between conductive layer 235 and position sensor array 236. The changing capacitance can be measured using a number of well-known circuit techniques, such as:

charge-sensitive amplifier;
impedance measurements in a bridge configuration (See, Bao et al., *Proc. Annu. Conf. Eng. Med. Biol.* 22, 119 (1980));
RC oscillators using a CMOS 555 timer. In effect this process converts the unknown capacitance into a time-constant by determining capacitance in an oscillator and measuring the frequency (M. R. Nueman et al., *IEEE Frontier Eng. Comp. Health Care Conf.* 436 (1984)); and
direct charge coupling such as using the moving plate as the gate of a field-effect transistor (W. Kuhnel et al., *Sensors and Actuators A*32, 560 (1992)).

Another position sensor embodiment utilizes the piezoelectric effect. As with a piezoelectric actuator, a piezoelectric position sensor includes a piezoelectric thin film deposited on both sides of the cantilever. Displacement of the cantilever is determined by measuring the strain-induced electric field on the piezoelectric thin film. The configuration of a piezoelectric position sensor is the same as the piezoelectric actuator shown in FIGS. 9A and 9B. However, the sensor area can be extended to cover the entire length of the cantilever, thereby increasing the deflection sensing capability. A piezoelectric displacement sensor has some unique advantages. In addition to large piezoelectric coupling, PZT has a large pyroelectric response and a large spontaneous polarization, which makes PZT a good candidate material for infrared (IR) detectors (See, D. Polla, *Ph.D. Dissertation*, Univ. of Cal., Berkeley, (1985)). If an IR scanning scope (for low light image acquisition) is needed, the same material can be used for light detection. Another advantage of this approach is that the material can also be used as the actuator.

A similar, but alternate position sensor embodiment uses a piezoresistive effect, which results in a change of carrier mobility as a function of stress. Effectively, a piezoresistance position sensor comprises a semiconductor strain gauge such as taught by J. J. Wortman et al., *IEEE Elect. Dev.* 16, 855 (1969); B. Puers et al., *IEEE Elect. Dev.* 35, 764 (1988) and S. R. Manalis, *Appl. Phys. Lett.* 69, 3944 (1996). The position sensor comprises electrically conducting, strain-sensitive regions that are fabricated by diffusing impurities, such as a boron dopant, into a highly resistive, single-crystal cantilever. For example, a p-type layer of boron can be diffused into an n-type silicon layer on the cantilever. The diffusion process preferably comprises open-tube boron diffusion from boron nitride, or boron ion plantation.

A bi-axial displacement sensor is illustrated in FIGS. 10A and 10B. More specifically, FIG. 10A is a side sectional view of a scanner with a piezoresistive transducer integrated into the cantilever. A vertical piezoresistive transducer 324 comprises a p-type diffused resistor that is oriented along the primary longitudinal axis of cantilever 212. Vertical piezoresistive transducer 324 detects vertical deflection (e.g., in a Z direction) of cantilever 212 relative to a primary plane of substrate 220. A horizontal piezoresistive transducer 326 also comprises a p-type diffused resistor, but is oriented along a secondary transverse axis of cantilever 212. Horizontal piezoresistive transducer 326 detects horizontal deflection (e.g., in a Y direction) of cantilever 212 relative to the primary plane of substrate 220. The magnitude of each displacement is calculated based on a fractional change in resistance $\Delta R/R$:

$$\Delta R/R = \pi_l T_l + \pi_t T_t$$

where $\pi_l$ and $\pi_t$ are longitudinal and transverse piezoresistance coefficients, and $T_l$ and $T_t$ are stresses parallel and perpendicular to the direction of current in the layer.

FIG. 10B is a plan view of the scanner with two piezoresistive transducers integrated into the cantilever. A p-type (e.g., boron doped) piezoresistor 320 is diffused into cantilever 212. Preferably, piezoresistor 320 is diffused into an n-type substrate such as silicon (e.g., with 100 surface orientation). Thus, a silicon cantilever can be used, or a silicon layer can be fabricated under a waveguide layer such as a layer of SU-8. A window is provided through the waveguide layer so that a conductive contact 322 can be connected to piezoresistor 320.

As indicated by functional blocks 54 and 84 of FIGS. 1A and 1B, respectively, other techniques can be used to provide a position sensor that can be integrated into a small area such as less than 3 mm. For example, light loss can be measured from waveguide bending. All waveguides lose light from their cores to the outside environment. In addition, a scanning waveguide also loses light to the environment in proportion to the deflection of the waveguide. This proportional loss is called bending loss. A device such as a photodetector or photodetector array that detects the quantity of light lost from the waveguide in proportion to the waveguide's motion can therefore measure the free end position of the waveguide. In near field scanning microscopes (NSOM), nanometer displacements of the tip of a waveguide are measured by introducing a beam of light that crosses the path of the actuated waveguide. Displacements along one axis is measured in relation to light loss or to light scatter in transmission through a waveguide or back to a nearby detector. Examples of the use of a laser diode and a photodiode in transmission for one axis are described by R. D. Grober, T. D. Harris, J. R. Tautman, and E. Betzig (1994), Design and implementation of a low temperature near-field scanning optical microscope, *Rev. Sci. Instrum.* 65(3): 626-631 and A. Shchemelinin, M. Rudman, K. Lieberman, and A. Lewis, (1993), A simple lateral force sensing technique for near-field micropattern generation, *Rev Sci Instrum.*, 64(12):3538-3541. An example of the use of an optical source and a detector in reflection mode from a vibrating cantilever is described by H. Muramatsu, N. Chiba, K. Homma, K. Nakajima, T. Ataka, S. Ohta, A. Kusumi and M. Fujihira (1995), Near-field optical microscopy in liquids, *Apl. Phys. Lett.* 66(24): 3245-3247. Optical detection of waveguide motion can be extended in 2-axes by implementing the single axis measurement in the orthogonal direction.

Alternatively, a ferromagnetic material can be deposited on the scanning waveguide, so that the free end position can be tracked with inductive coils. Conversely, a magnetic sensor can detect a change in magnetic field. As another alternative, an integrated, dual axis interferometer can be used to detect the vertical and horizontal position of the free end of the waveguide. A piezoresistive sensor can also be used in the cantilever to detect position. If space is available, a quadrant fiber bundle can be used to detect light provided from the free end of the waveguide. Additionally, the actuator itself can be used to detect position.

Light Detectors

As illustrated in FIG. 3, photon detectors 224a and 224b detect light backscattered from the target in the ROI. Similarly, photodiode 246 shown in FIG. 5 detects light directed back through the cantilever waveguide. Preferably, these light detectors are of the same wavelength spectrum or the same red, green, blue (RGB) spectrums. The light detectors are also preferably constructed from a silicon substrate, which can be the material used in the waveguide, actuator, coupler and displacement sensor. A silicon photodiode is known for light wave detection in the wavelength ranges of 0.4 μm to 1 μm due to silicon's high responsiveness near that wavelength spectrum. Silicon also has the virtues of high quantum efficiency, good linearity of response, large bandwidth, simple bias option, and relatively low cost. There are several methods for integrating an optical detector on a silicon substrate. A common type of optical detector is a depletion-layer photodiode. The depletion-layer photodiode is essentially a reverse-biased semiconductor diode, wherein reverse current is modulated by electron-hole pairs produced in or near the depletion layer by the absorption of photons. The simplest depletion layer photodiode is a p-n junction diode.

As an alternative to using a conventional mesa-geometry photodiode configuration for the light detector, the diode can be hybridized with a waveguide and a fiber detector to optimize the intensity absorption. As illustrated by FIG. 6A, the backscattered light is first captured by single optical fiber 256 or a fiber bundle detector. Then the light is inserted into waveguide 260 through a grating or mechanical coupler 258 such as a V-groove and/or silicon nitride clips. The light is directed to the other end of the waveguide where the light is received by photon detector 262, which is preferably a silicon photodiode. The diode can be formed by boron diffusion to a n-type silicon substrate in a manner similar to that described above with regard to the piezoresistor and/or as described by D. Ostrowsky et al., *App. Phys. Lett.* 22 (1973). A thick layer (several micrometers) of waveguide material made of either $SiO_2$ or silicon nitride can also be grown and used as a diffusion mask and later left as the waveguide. Metal electrodes are added to complete the structure. The benefit of having the fiber detector is that it allows the photodetector to be at the proximal end of the probe without actually having the photodiode placed near the probe. In this hybrid design, the photodiode is less affected by noise and environmental factors. The fiber can also be coated with metal and bent to a desired viewpoint. In addition, a separate support can be used to stabilize the tip of the fiber during high resolution imaging.

In any case, the small detecting area on the diode (approximately few tens of microns in diameter) provides giga hertz (GHz) range bandwidth. Also, since pairs of red, green, and blue photodetectors are required for capturing a color image, these silicon-based photodiodes can offer sufficient bandwidth in the visible spectrum (e.g., the photodetector bandwidths must exceed 12.5 MHz for VGA and 19.8 MHz for SVGA video standard). To improve the overall wavelength response with modest bias, an intrinsic region of high resistivity can be added to the p-n junction to form a so-called PIN structure. To obtain a high current gain and maintain a high operating frequency, an avalanche photodetector (APD) structure can be implemented, such as that described by P. P. Webb, *IEEE solid state sensors symposium.* 96 (1970). In this device, a basic p-n structure is operated under a very high reverse bias. By setting the bias precisely at the point of avalanche breakdown, carrier multiplication due to impact ionization can result in significant gain in terms of increase in the carrier to photon ratio. The current multiplication for an avalanche diode can be as high as 4 orders of magnitude (based on commercially available photovoltaic photodiode and APD from UDT Sensor LTD).

Although the present invention has been described in connection with the preferred form of practicing it and modifications thereto, those of ordinary skill in the art will understand that many other modifications can be made to the present invention within the scope of the claims that follow. For example, modular components can be constructed separately, each with an optimal substrate. The modular components can then be bonded together using anodic, adhesive, or other bonding methods. Accordingly, it is not intended that The invention in which an exclusive right is claimed is defined by the following:

1. An apparatus for display of an image, in regard to a limited region of interest, wherein the apparatus is configured as a micro-electro-mechanical system (MEMS), comprising:
   (a) a light source comprising an emitter layer which emits light;
   (b) a support substrate;
   (c) a cantilever comprising a fixed end and a free end, the fixed end is supported by the support substrate, the fixed end remaining fixed to the support substrate and the free end extending freely relative to the support substrate, enabling the free end to bend and deflect in regard to the limited region of interest, the bending of the cantilever scanning light onto an image plane to create an image, wherein the cantilever is configured as one of:
      (i) a waveguide that conveys light from the light source within the cantilever, when scanning the light onto the image plane to create the image, the cantilever comprising a material having an optical property configured to convey the light within the cantilever; and
      (ii) a moving carrier for the light source comprising the emitter layer that emits the light, the light source being mounted on the free end of the cantilever and moving when scanning the light emitted by the light source onto the image plane to create the image; and
   (d) an actuator disposed adjacent to the cantilever and being employed for deflecting the cantilever so as to move the free end to scan in a desired motion.

2. The apparatus of claim 1, wherein the light source is end-butted to the fixed end of the cantilever.

3. The apparatus of claim 1, wherein the actuator comprises at least one of:
   (a) an actuator for deflecting the cantilever in a vertical direction relative to a primary plane of the support substrate; and
   (b) an actuator for deflecting the cantilever in a horizontal direction relative to the primary plane of the support substrate.

4. The apparatus of claim 1, further comprising a position sensor employed for detecting a position of the free end of the cantilever, for producing a signal used in controlling the actuator to cause the cantilever to move in the desired motion, wherein the position sensor comprises one of the group consisting of:
   (a) the actuator;
   (b) a piezoelectric transducer;
   (c) a capacitive displacement transducer;
   (d) a piezoresistive sensor;
   (e) a light source and detector pair;
   (f) a photodetector array;
   (g) a magnetic sensor;
   (h) a fiber bundle displacement sensor;
   (i) an interferometer; and
   (j) an inductive displacement transducer.

5. The apparatus of claim 1, further comprising a lens disposed at the free end of the cantilever through which the light conveyed through the cantilever passes.

6. An apparatus for use either for a far-field image acquisition or for a display of an image, in regard to a limited region of interest comprising a target, wherein the apparatus is configured as a micro-electro-mechanical system (MEMS), the apparatus comprising:
   (a) a light source comprising an emitter layer which emits light;
   (b) a substrate that serves as a support;
   (c) a cantilever comprising at least one of a thin film layer and a thick film layer and having a fixed end and a free end, the fixed end remaining fixed to a proximal end of the substrate upon which the cantilever was originally formed and the free end extending freely beyond where the substrate has been removed from supporting the cantilever, enabling the free end to bend and deflect relative to the substrate and the limited region of interest, for scanning with the free end of the cantilever relative to the target, at least one of the thin film layer or the thick film layer comprising a material having an optical property configured to convey the light within the cantilever; and
   (d) an actuator disposed adjacent to the cantilever, the actuator being employed for bending and deflecting the cantilever so as to move the free end in a desired motion, to scan at least a portion of the limited region of interest.

7. The apparatus of claim 6, wherein the light source provides the light using at least one of a diode, a laser, and an optical fiber.

8. The apparatus of claim 6, further comprising a photon detector configured to receive light at a location that is proximate to the cantilever and to the support.

9. The apparatus of claim 6, wherein the cantilever comprises one of:
   (a) an emitting waveguide that receives the light at the fixed end and directs the light received to the free end, where the light is emitted for illuminating the target;
   (b) a receiving waveguide that receives light that is reflected from the target through the free end and directs the received light to the fixed end for detection by the photon detector; and
   (c) a flexible member that supports the light source.

10. The apparatus of claim 6, wherein the cantilever is deflected by the actuator to have a motion selected from a group of motions consisting of:
   (a) a resonant motion in at least one of two directions;
   (b) a non-resonant motion in at least one of the two directions;
   (c) a two-dimensional circular motion using a single actuator;
   (d) a two-dimensional rocking linear motion using a single actuator; and
   (e) a motion that selectively moves the free end to a desired position.

11. A method for enabling either a far-field image acquisition or a display of an image, in regard to a limited region of interest, using a micro-electro-mechanical system (MEMS), comprising the steps of
   (a) providing a cantilever on a substrate, wherein a portion of the substrate underlying the cantilever is removed, the cantilever comprising a material having an optical property configured to convey light within the cantilever;
   (b) supporting the cantilever at a fixed end of the cantilever, the fixed end remaining fixed to the substrate, a free end of the cantilever extending freely beyond where the portion of the substrate was removed from supporting the cantilever, enabling the free end to bend and deflect relative to a target in the limited region of interest, for scanning the target;
   (c) bending and deflecting the cantilever so as to move the free end in a desired motion to scan the target; and (d) receiving light from a light source comprising an emitter layer, the light source positioned at a location that is proximate to the cantilever and to the support.

12. The method of claim 11, further comprising the step of detecting a position of the free end of the cantilever, producing a signal indicative of the position for use in controlling the cantilever to move in the desired motion.

13. The method of claim 11, further comprising the step of forming the cantilever by at least one of a deep reactive ion etching and a wet anisotropic etching of the substrate using a mask to define a shape of the cantilever.

14. The method of claim 11, further comprising at least one of the steps of:
  (a) receiving light at the fixed end and directing the light received to the free end, said cantilever acting as a waveguide, said free end emitting light to illuminate the target;
  (b) receiving light that is reflected from the target through the free end and directing the light that is received to the fixed end for detection by a photon detector; and
  (c) supporting a light source at the free end, said light source emitting light that illuminates the target.

15. The method of claim 11, wherein the step of sensing the position of the cantilever is done with one of the group consisting of
  (a) an actuator, when the actuator is not being employed for driving the cantilever to move in the desired motion;
  (b) a piezoelectric transducer;
  (c) a capacitive displacement transducer;
  (d) a piezoresistive sensor;
  (e) a light source and detector pair;
  (f) a photodetector array;
  (g) a magnetic sensor;
  (h) a fiber bundle displacement sensor;
  (i) an interferometer; and
  (j) an inductive displacement transducer.

16. The method of claim 11, wherein the step of deflecting the cantilever comprises the step of driving the free end of the cantilever to move in a pattern relative to the target so as to do one of the steps of:
  (a) displaying an image on the target; and
  (b) acquiring an image of the target.

\* \* \* \* \*